United States Patent
Müller et al.

(10) Patent No.: US 6,610,631 B1
(45) Date of Patent: Aug. 26, 2003

(54) SUBSTITUTED ARYL KETONES

(75) Inventors: Klaus-Helmut Müller, Düsseldorf (DE); Stefan Lehr, Langenfeld (DE); Otto Schallner, Monheim (DE); Hans-Georg Schwarz, Langenfeld (DE); Mark Wilhelm Drewes, Langenfeld (DE); Peter Dahmen, Neuss (DE); Dieter Feucht, Monheim (DE); Rolf Pontzen, Leichlingen (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/089,293

(22) PCT Filed: Sep. 18, 2000

(86) PCT No.: PCT/EP00/09090
§ 371 (c)(1),
(2), (4) Date: Mar. 27, 2002

(87) PCT Pub. No.: WO01/23367
PCT Pub. Date: Apr. 5, 2001

(30) Foreign Application Priority Data

Sep. 30, 1999 (DE) ......................... 199 46 853

(51) Int. Cl.⁷ ..................... A01N 43/647; C07D 249/02
(52) U.S. Cl. ..................... 504/273; 548/264.4
(58) Field of Search .................. 548/264.4; 504/273

(56) References Cited

U.S. PATENT DOCUMENTS

| | | | |
|---|---|---|---|
| 3,742,014 A | 6/1973 | Grivsky | 260/465 B |
| 3,767,666 A | 10/1973 | Zielinski | 260/308 C |
| 3,978,127 A | 8/1976 | Engelhardt et al. | 260/570.5 R |
| 4,098,896 A | * 7/1978 | Edwards | 424/269 |
| 4,542,127 A | 9/1985 | Hitzel et al. | 514/161 |
| 4,780,127 A | 10/1988 | Michaely et al. | 71/103 |
| 4,806,146 A | 2/1989 | Carter | 71/98 |
| 4,816,066 A | 3/1989 | Michaely et al. | 71/123 |
| 4,837,333 A | 6/1989 | Manley et al. | 548/341 |
| 4,946,981 A | 8/1990 | Carter et al. | 558/415 |
| 4,986,845 A | 1/1991 | Oya et al. | 71/92 |
| 5,006,158 A | 4/1991 | Carter et al. | 71/98 |
| 5,085,688 A | 2/1992 | Michaely et al. | 71/103 |
| 5,110,343 A | 5/1992 | Ueda et al. | 71/88 |
| 5,171,748 A | 12/1992 | Roberts et al. | 514/381 |
| 5,185,351 A | 2/1993 | Finkelstein et al. | 514/341 |
| 5,189,033 A | 2/1993 | Tucker | 514/211 |
| RE34,779 E | 11/1994 | Oya et al. | 504/282 |
| 5,371,063 A | 12/1994 | Cramp et al. | 504/270 |
| 5,374,606 A | 12/1994 | Cramp et al. | 504/270 |
| 5,418,250 A | 5/1995 | Finkelstein et al. | 514/397 |
| 5,489,570 A | 2/1996 | Geach et al. | 504/261 |
| 5,650,533 A | 7/1997 | Roberts et al. | 560/17 |
| 5,656,573 A | 8/1997 | Roberts et al. | 504/271 |
| 5,747,424 A | 5/1998 | Roberts et al. | 504/271 |
| 5,804,532 A | 9/1998 | Cain et al. | 504/309 |
| 5,834,402 A | 11/1998 | Von Deyn et al. | 504/271 |
| 5,846,906 A | 12/1998 | von Deyn et al. | 504/221 |
| 5,846,907 A | 12/1998 | von Deyn et al. | 504/221 |
| 5,859,283 A | 1/1999 | Cramp | 560/124 |
| 5,863,865 A | 1/1999 | Lee et al. | 504/271 |
| 5,880,147 A | 3/1999 | Yoshida et al. | 514/452 |
| 5,948,917 A | 9/1999 | Adachi et al. | 548/247 |
| 6,004,903 A | 12/1999 | von Deyn et al. | 504/239 |
| 6,040,339 A | 3/2000 | Yoshida et al. | 514/485 |
| 6,063,789 A | 5/2000 | Hamley et al. | 514/301 |
| 6,124,469 A | 9/2000 | Rheinheimer et al. | 548/240 |
| 6,153,759 A | 11/2000 | von Deyn et al. | 548/131 |
| 6,165,944 A | 12/2000 | von Deyn et al. | 504/271 |
| 6,297,198 B1 | 10/2001 | Lee | 504/271 |
| 2002/0025910 A1 | 2/2002 | WOX | 504/263 |

FOREIGN PATENT DOCUMENTS

| | | |
|---|---|---|
| CA | 2220494 | 11/1996 |
| CA | 2252543 | 11/1997 |
| DE | 196 27 901 | 1/1998 |
| DE | 199 21 732 | 1/2000 |
| EP | 093 488 | 11/1983 |
| EP | 186 119 | 8/1989 |
| EP | 527 036 | 11/1996 |
| GB | 1451299 | 9/1976 |
| WO | 97/27187 | 7/1997 |
| WO | 97/41105 | 11/1997 |
| WO | 97/41116 | 11/1997 |
| WO | 97/41117 | 11/1997 |
| WO | 97/46530 | 12/1997 |
| WO | 98/28981 | 7/1998 |
| WO | 99/03856 | 1/1999 |
| WO | 99/07688 | 2/1999 |

OTHER PUBLICATIONS

**Chemical Abstracts, vol. 127, No. 2, Jul. 14, 1997, Abstract No. 14448, XP002157912, Y. Yamada et al, "Herbicide mixtures containing benzoyl cyclic enon derivatives for rice paddies", Zusammenfassung & JP 09 104604 A (SDS Biotech Corp), Apr. 22, 1997.
J. Med. Chem, 35, (month available), 1992, pp. 2573–2581, Martin J. Drysdale et al,.
"Rationally Designed "Dipeptoid Analogues" Analogues of CCK. Acid Memics of the Potent and Selective Non–Peptide CCK–B Receptor Antagoinist CI–988".

* cited by examiner

Primary Examiner—Joseph K. McKane
Assistant Examiner—Golam M. M. Shameem
(74) Attorney, Agent, or Firm—Richard E. L. Henderson; John E. Mrozinski, Jr.

(57) ABSTRACT

The invention relates to novel substituted aryl ketones of the general formula (I)

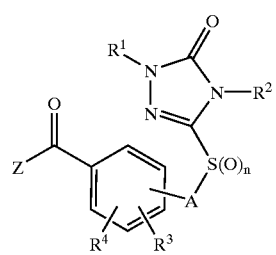

(I)

in which
  n, A, $R^1$, $R^2$, $R^3$, $R^4$ and Z are each as defined in the description,
to processes for their preparation and to their use as herbicides.

8 Claims, No Drawings

SUBSTITUTED ARYL KETONES

This application is a 371 of PCT/EP00/09090 Sep. 18, 2000.

FIELD OF THE INVENTION

The invention relates to novel substituted aryl ketones, to processes for their preparation and to their use as herbicides.

BACKGROUND OF THE INVENTION

It is already known that certain substituted aryl ketones have herbicidal properties (cf. EP-A-090 262, EP-A-135 191, EP-A-186 118, EP-A-186 119, EP-A-186 120, EP-A-319 075, EP-A-352 543, EP-A-418 175, EP-A-487 357, EP-A-527 036, EP-A-527 037, EP-A-560 483, EP-A-609 797, EP-A-609 798, EP-A-625 505, EP-A-625 508, EP-A-636 622, U.S. Pat. No. 5,804,532, U.S. Pat. No. 5,834,402, U.S. Pat. 5,846,906, U.S. Pat. No. 5,863,865, WO-A-96/26192, WO-A-96/26193, WO-A-96/26200, WO-A-96126206, WO-A-97/27187, WO-A-97/35850, WO-A-97/41105, WO-A-97/41116, WO-A-97/41117, WO-A-97/41118, WO-A-97/43270, WO-A-97/46530, WO-A-98/28981, WO-A-98/31681, WO-A-98/31682, WO-A-99/03856, WO-A-99/07688). However, the activity of these compounds is not entirely satisfactory.

DETAILED DESCRIPTION OF THE INVENTION

This invention, accordingly, provides the novel substituted aryl ketones of the general formula (I)

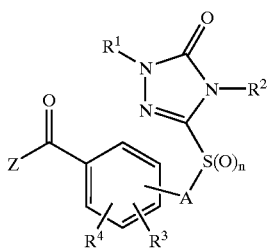

(I)

in which
  n represents the numbers 0, 1 or 2,
  A represents a single bond or represents alkanediyl,
  $R^1$ represents hydrogen or represents in each case optionally substituted alkyl, alkenyl, alkinyl, cycloalkyl, cycloalkylalkyl, aryl or arylalkyl,
  $R^2$ represents hydrogen, amino, or represents in each case optionally substituted alkyl, alkoxy, alkylamino, dialkylamino, alkenyl, alkenyloxy, alkinyl, alkinyloxy, cycloalkyl, cycloalkylalkyl, aryl, arylamino or arylalkyl,
  $R^3$ represents hydrogen, nitro, cyano, carboxyl, carbamoyl, thiocarbamoyl, halogen, or represents in each case optionally substituted alkyl, alkylcarbonyl, alkoxy, alkoxycarbonyl, alkylthio, alkylsulphinyl, alkylsulphonyl, alkyl-amino, dialkylamino or dialkylaminosulphonyl,
  $R^4$ represents hydrogen, nitro, cyano, carboxyl, carbamoyl, thiocarbamoyl, halogen, or represents in each case optionally substituted alkyl, alkylcarbonyl, alkoxy, alkoxycarbonyl, alkylthio, alkylsulphinyl, alkylsulphonyl, alkyl-amino, dialkylamino or dialkylaminosulphonyl, and Z represents one of the groupings below

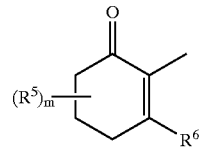 (Z¹)

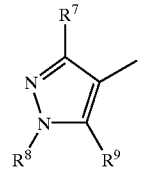 (Z²)

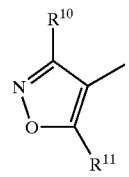 (Z³)

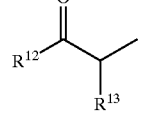 (Z⁴)

where
  m represents the numbers 0 to 6,
  $R^5$ represents halogen or represents in each case optionally substituted alkyl or alkylthio, or—if m represents 2-together with a second radical $R^5$ represents alkanediyl (alkylene),
  $R^6$ represents hydroxyl, formyloxy, or represents in each case optionally substituted alkoxy, alkylthio, alkylcarbonyloxy, alkoxycarbonyloxy, alkylaminocarbonyloxy, alkylsulphonyloxy, alkenyloxy, alkinyloxy, arylalkyl, aryloxy, arylthio, arylcarbonyloxy, arylcarbonylalkoxy, arylsulphonyloxy, arylalkoxy or arylalkylthio,
  $R^7$ represents hydrogen, cyano, carbamoyl, thiocarbamoyl, halogen, or represents in each case optionally substituted alkyl, alkoxy, alkylthio, alkylsulphinyl, alkylsulphonyl, alkoxycarbonyl or cycloalkyl,
  $R^8$ represents hydrogen or represents in each case optionally substituted alkyl, alkenyl, alkinyl, cycloalkyl, cycloalkylalkyl, aryl or arylalkyl,
  $R^9$ represents hydroxyl, formyloxy, or represents in each case optionally substituted alkoxy, alkylcarbonyloxy, alkoxycarbonyloxy, alkylaminocarbonyloxy, alkylsulphonyloxy, alkenyloxy, alkinyloxy, arylalkoxy, arylcarbonyloxy, arylcarbonylalkoxy or arylsulphonyloxy,
  $R^{10}$ represents hydrogen, cyano, carbamoyl, thiocarbamoyl, halogen, or represents in each case optionally substituted alkyl, alkylcarbonyl, alkoxy, alkoxy-carbonyl or alkylthio,
  $R^{11}$ represents hydrogen or represents in each case optionally substituted alkyl or cycloalkyl,
  $R^{12}$ represents hydrogen or represents in each case optionally substituted alkyl or cycloalkyl, and $R^{13}$ represents hydrogen, cyano, carbamoyl, halogen, or represents in each case optionally substituted alkyl, alkoxy, alkoxycarbonyl, alkylthio, alkylsulphinyl or alkylsulphonyl, including all possible tautomeric forms of the compounds of the general formula (I) and the possible salts of the compounds of the general formula (I).

In the definitions, the hydrocarbon chains, such as alkyl or alkanediyl, are in each case straight-chain or branched—including in combination with heteroatoms, such as in alkoxy.

Preferred substituents and preferred ranges of the radicals present in the formulae mentioned above and belong are defined below.

A preferably represents a single bond or represents alkanediyl having 1 to 6 carbon atoms.

$R^1$ preferably represents hydrogen, represents optionally cyano-, halogen- or $C_1$–$C_4$-alkoxy-substituted alkyl having 1 to 6 carbon atoms, represents in each case optionally cyano- or halogen-substituted alkenyl or alkinyl having in each case 2 to 6 carbon atoms, represents in each case optionally cyano-, halogen- or $C_1$–$C_4$-alkyl-substituted cycloalkyl or cycloalkylalkyl having in each case 3 to 6 carbon atoms in the cycloalkyl group and optionally 1 to 4 carbon atoms in the alkyl moiety, or represents in each case optionally nitro-, cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted aryl or arylalkyl having in each case 6 or 10 carbon atoms in the aryl group and optionally 1 to 4 carbon atoms in the alkyl moiety.

$R^2$ preferably represents hydrogen, amino, represents in each case optionally cyano-, halogen- or $C_1$–$C_4$-alkoxy-substituted alkyl, alkoxy, alklylamino or di-alkylamino having in each case 1 to 6 carbon atoms in the alkyl groups, represents in each case optionally cyano- or halogen-substituted alkenyl, alkenyloxy, alkinyl or alkinyloxy having in each case 2 to 6 carbon atoms, represents in each case optionally cyano-, halogen- or $C_1$–$C_4$-alkyl-substituted cycloalkyl or cycloalkylalkyl having in each case 3 to 6 carbon atoms in the cycloalkyl group and optionally 1 to 4 carbon atoms in the alkyl moiety, or represents in each case optionally nitro-, cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted aryl, arylamino or arylalkyl having in each case 6 or 10 carbon atoms in the aryl group and optionally 1 to 4 carbon atoms in the alkyl moiety.

$R^3$ preferably represents hydrogen, nitro, cyano, carboxyl, carbamoyl, thio-carbamoyl, halogen, or represents in each case optionally cyano-, halogen- or $C_1$–$C_4$-alkoxy-substituted alkyl, alkylcarbonyl, alkoxy, alkoxycarbonyl, alkylthio, alkylsulphinyl, alkylsulphonyl, alkylamino, dialkylamino or dialkylaminosulphonyl having in each case 1 to 6 carbon atoms in the alkyl groups.

$R^4$ preferably represents hydrogen, nitro, cyano, carboxyl, carbamoyl, thio-carbamoyl, halogen, or represents in each case optionally cyano-, halogen- or $C_1$–$C_4$-alkoxy-substituted alkyl, alkylcarbonyl, alkoxy, alkoxycarbonyl, alkylthio, alkylsulphinyl, alkylsulphonyl, alkylamino, dialkylamino or dialkylaminosulphonyl having in each case 1 to 6 carbon atoms in the alkyl groups.

m preferably represents the numbers 0, 1, 2, 3 or 4.

$R^5$ preferably represents halogen or represents in each case optionally cyano-, halogen- or $C_1$–$C_4$-alkoxy-substituted alkyl or alkylthio having in each case 1 to 6 carbon atoms, or optionally also—if m represents 2—together with a second radical $R^5$ represents alkanediyl (alkylene) having 2 to 6 carbon atoms.

$R^6$ preferably represents hydroxyl, formyloxy, or represents in each case optionally cyano-, halogen- or $C_1$–$C_4$-alkoxy-substituted alkoxy, alkylthio, alkylcarbonyloxy, alkoxycarbonyloxy, alkylaminocarbonyloxy or alkyl-sulphonyloxy having in each case 1 to 6 carbon atoms in the alkyl groups, represents in each case optionally cyano- or halogen-substituted alkenyloxy or alkinyloxy having in each case 2 to 6 carbon atoms, or represents in each case optionally nitro-, cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted arylalkyl, aryloxy, arylthio, arylcarbonyloxy, arylcarbonylalkoxy, arylsulphonyloxy, arylalkoxy or arylalkylthio having in each case 6 or 10 carbon atoms in the aryl group and optionally 1 to 4 carbon atoms in the alkyl moiety.

$R^7$ preferably represents hydrogen, cyano, carbamoyl, thiocarbamoyl, halogen, represents in each case optionally cyano-, halogen- or $C_1$–$C_4$-alkoxy-substituted alkyl, alkoxy, alkylthio, alkylsulphinyl, alkylsulphonyl or alkoxy-carbonyl having in each case 1 to 6 carbon atoms in the alkyl groups, or represents optionally cyano-, halogen- or $C_1$–$C_4$-alkyl-substituted cycloalkyl having 3 to 6 carbon atoms.

$R^8$ preferably represents hydrogen, represents in each case optionally cyano-, halogen- or $C_1$–$C_4$-alkoxy-substituted alkyl having 1 to 6 carbon atoms, represents in each case optionally cyano- or halogen-substituted alkenyl or alkinyl having in each case 2 to 6 carbon atoms, represents in each case optionally cyano-, halogen- or $C_1$–$C_4$-alkyl-substituted cycloalkyl or cycloalkylalkyl having in each case 3 to 6 carbon atoms in the cycloalkyl group and optionally 1 to 4 carbon atoms in the alkyl moiety, or represents in each case optionally nitro-, cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted aryl or arylalklyl having in each case 6 or 10 carbon atoms in the aryl group and optionally 1 to 4 carbon atoms in the alkyl moiety.

$R^9$ preferably represents hydroxyl, formyloxy, represents in each case optionally cyano-, halogen- or $C_1$–$C_4$-alkoxy-substituted alkoxy, alkylcarbonyloxy, alkoxycarbonyloxy, alkylaminocarbonyloxy or alkylsulphonyloxy having in each case 1 to 6 carbon atoms in the alkyl groups, represents in each case optionally cyano- or halogen-substituted alkenyloxy or alkinyloxy having in each case 2 to 6 carbon atoms, or represents in each case optionally nitro-, cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted arylalkoxy, arylcarbonyloxy, arylcarbonyl-alkoxy or arylsulphonyloxy having in each case 6 or 10 carbon atoms in the aryl group and optionally 1 to 4 carbon atoms in the alkyl moiety.

$R^{10}$ preferably represents hydrogen, cyano, carbamoyl, thiocarbamoyl, halogen, or represents in each case optionally cyano-, halogen- or $C_1$–$C_4$-alkoxy-substituted alkyl, alkylcarbonyl, alkoxy, alkoxycarbonyl or alkylthio having in each case 1 to 6 carbon atoms in the alkyl groups.

$R^{11}$ preferably represents hydrogen, represents optionally cyano-, halogen- or $C_1$–$C_4$-alkoxy-substituted alkyl having 1 to 6 carbon atoms or represents optionally cyano-, halogen- or $C_1$–$C_4$-alkyl-substituted cycloalkyl having 3 to 6 carbon atoms.

$R^{12}$ preferably represents hydrogen, represents optionally cyano-, halogen- or $C_1$–$C_4$-alkoxy-substituted alkyl having 1 to 6 carbon atoms or represents optionally cyano-, halogen- or $C_1$–$C_4$-alkyl-substituted cycloalkyl having 3 to 6 carbon atoms.

$R^{13}$ preferably represents hydrogen, cyano, carbamoyl, halogen, or represents in each case optionally cyano-, halogen- or $C_1$–$C_4$-alkloxy-substituted alkyl, alkoxy, alkoxycarbonyl, alkylthio, alkylsulphinyl or alkylsulphonyl having in each case 1 to 6 carbon atoms in the alkyl groups.

A particularly preferably represents a single bond or represents alkanediyl having 1 to 4 carbon atoms.

$R^1$ particularly preferably represents hydrogen, represents in each case optionally cyano-, fluorine-, chlorine-, methoxy- or ethoxy-substituted methyl, ethyl, n- or i-propyl, n-, i-, s- or t-butyl, represents in each case optionally cyano-, fluorine-, chlorine- or bromine-substituted propenyl, butenyl, propinyl or butinyl, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexyl-methyl, or represents in each case optionally nitro-, cyano-, fluorine-, chlorine-, bromine-, methyl-, ethyl-, n- or i-propyl-, n-, i-, s- or t-butyl-, tri-fluoromethyl-, methoxy-, ethoxy-, n- or i-propoxy-, n-, i-, s- or t-butoxy-, di-fluoromethoxy- or trifluoromethoxy-substituted phenyl, benzyl or phenylethyl.

$R^2$ particularly preferably represents hydrogen, amino, represents in each case optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i- or s-butylamino, dimethylamino or diethylamino, represents in each case optionally cyano-, fluorine-, chlorine- or bromine-substituted propenyl, butenyl, propenyloxy, butenyloxy, propinyl, butinyl, propinyloxy or butinyloxy, represents in each case optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoro-methyl-, methoxy-, ethoxy-, n- or i-propoxy-, n-, i-, s- or t-butoxy-, difluoromethoxy- or trifluoromethyloxy-substituted phenyl, phenylamino, benzyl or phenylethyl.

$R^3$ particularly preferably represents hydrogen, nitro, cyano, carboxyl, carbamoyl, thiocarbamoyl, fluorine, chlorine, bromine, or represents in each case optionally cyano-, fluorine-, chlorine-, methoxy- or ethoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n-or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, di-methylamino, diethylamino, dimethylaminosulphonyl or diethylamino-sulphonyl.

$R^4$ particularly preferably represents hydrogen, nitro, cyano, carboxyl, carbamoyl, thiocarbamoyl, fluorine, chlorine, bromine, or represents in each case optionally cyano-, fluorine-, chlorine-, methoxy- or ethoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n-or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, di-methylamino, diethylamino, dimethylaminosulphonyl or diethylamino-sulphonyl.

m particularly preferably represents the numbers 0, 1, 2 or 3.

$R^5$ particularly preferably represents fluorine, chlorine, bromine, or represents in each case optionally cyano-, fluorine-, chlorine-, methoxy- or ethoxy-substituted methyl, ethyl, n- or i-propyl, n-, i-, s- or t-butyl, methylthio, ethylthio, n- or i-propylthio, n-, i-, s- or t-butylthio, or optionally also—if m represents 2—together with a second radical $R^5$ represents ethane-1,2-diyl (di-methylene), propane-1,3-diyl (trimethylene) or butane-1,4-diyl (tetra-methylene).

$R^6$ particularly preferably represents hydroxyl, formyloxy, represents in each case optionally cyano-, fluorine-, chlorine-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, acetyloxy, propionyloxy, n- or i-butyroyloxy, methoxycarbonyloxy, ethoxycarbonyloxy, n- or i-propoxy-carbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally cyano-, fluorine-, chlorine- or bromine-substituted propenyloxy, butenyloxy, propinyloxy or butinyloxy, or represents in each case optionally nitro-, cyano-, fluorine-, chlorine-, bromine-, methyl-, ethyl-, n- or i-propyl-, n-, i-, s- or t-butyl-, tri-fluoromethyl-, methoxy-, ethoxy-, n- or i-propoxy-, n-, i-, s- or t-butoxy-, di-fluoromethoxy- or trifluoromethoxy-substituted phenoxy, phenylthio, benzoyloxy, benzoylmethoxy, phenylsulphonyloxy, phenylmethoxy, phenyl-methylthio or benzyl.

$R^7$ particularly preferably represents hydrogen, cyano, carbamoyl, thio-carbamoyl, fluorine, chlorine, bromine, represents in each case optionally cyano-, fluorine-, chlorine-, methoxy- or ethoxy-substituted methyl, ethyl, n-or i-propyl, n-, i-, s- or t-butyl, methoxy, ethoxy, n- or i-propoxy, n-, i-, s- or t-butoxy, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methoxycarbonyl, ethoxycarbonyl, n- or i-propoxycarbonyl, or represents in each case optionally cyano-, fluorine-, chlorine-, bromine-, methyl- or ethyl-substituted cyclopropyl, cyclobutyl, cyclopentyl or cyclohexyl.

$R^8$ particularly preferably represents hydrogen, represents in each case optionally cyano-, fluorine-, chlorine-, bromine-, methoxy- or ethoxy-substituted methyl, ethyl, n- or i-propyl, n-, i-, s- or t-butyl, represents in each case optionally cyano-, fluorine-, chlorine- or bromine-substituted propenyl, butenyl, propinyl or butinyl, represents in each case optionally cyano-, fluorine-, chlorine-, bromine-, methyl- or ethyl-substituted cyclopropyl, cyclobutyl, cyclopentyl, cyclohexyl, cyclopropylmethyl, cyclobutylmethyl, cyclopentyl-methyl or cyclohexylmethyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl or benzyl.

$R^9$ particularly preferably represents hydroxyl, formyloxy, represents in each case optionally cyano-, fluorine-, chlorine-, bromine-, methoxy-, ethoxy-, n- or i-propoxy-substituted methoxy, ethoxy, n- or i-propoxy, n-, i-, s- or t-butoxy, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents in each case optionally cyano-, fluorine-, chlorine- or bromine-substituted propenyloxy, butenyloxy, propinyloxy or butinyloxy, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl-methoxy, benzoyloxy, benzoylmethoxy or phenylsulphonyloxy.

$R^{10}$ particularly preferably represents hydrogen, cyano, carbamoyl, thio-carbamoyl, fluorine, chlorine, bromine, or represents in each case optionally cyano-, fluorine-, chlorine-, bromine-, methoxy-, ethoxy-, n- or i-propoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio.

$R^{11}$ particularly preferably represents hydrogen, represents in each case optionally cyano-, fluorine-, chlorine-, bromine-, methoxy- or ethoxy-substituted methyl, ethyl, n- or i-propyl, n-, i-, s- or t-butyl, or represents in each case optionally cyano-, fluorine-, chlorine-, bromine-, methyl- or ethyl-substituted cyclopropyl, cyclobutyl, cyclopentyl or cyclohexyl.

$R^{12}$ particularly preferably represents hydrogen, represents in each case optionally cyano-, fluorine-, chlorine-, bromine-, methoxy- or ethoxy-substituted methyl, ethyl, n- or i-propyl, n-, i-, s- or t-butyl, or represents in each case optionally cyano-, fluorine-, chlorine-, bromine-, methyl- or ethyl-substituted cyclopropyl, cyclobutyl, cyclopentyl or cyclohexyl.

$R^{13}$ particularly preferably represents hydrogen, cyano, carbamoyl, fluorine, chlorine, bromine, or represents in each case optionally cyano-, fluorine-, chlorine-, bromine-, methoxy- or ethoxy-substituted methyl, ethyl, n- or i-propyl, n-, i-, s- or t-butyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl.

A very particularly preferably represents a single bond or represents methylene ($CH_2$), dimethylene (ethane-1,2-diyl, —$CH_2CH_2$—) or ethylidene (ethane-1,1-diyl, —$CH(CH_3)$—).

$R^1$ very particularly preferably represents hydrogen, represents in each case optionally cyano-, fluorine-, chlorine-, methoxy- or ethoxy-substituted methyl, ethyl, n- or i-propyl, represents in each case optionally fluorine- or chlorine-substituted propenyl, butenyl, propinyl or butinyl, represents in each case optionally fluorine-, chlorine- or methyl-substituted cyclopropyl or cyclopropylmethyl, or represents in each case optionally fluorine-, chlorine-, bromine-, methyl-, trifluoromethyl-, methoxy-, difluoromethoxy- or trifluoro-methoxy-substituted phenyl or benzyl.

$R^2$ very particularly preferably represents hydrogen, amino, represents in each case optionally cyano-, fluorine-, chlorine-, methoxy- or ethoxy-substituted methyl, ethyl, n- or i-propyl, methoxy, ethoxy, n- or i-propoxy, methylamino, ethylamino, n- or i-propylamino, dimethylamino or diethylamino, represents in each case optionally fluorine- or chlorine-substituted propenyl, butenyl, propinyl or butinyl, represents in each case optionally fluorine-, chlorine- or methyl-substituted cyclopropyl or cyclopropylmethyl, or represents in each case optionally fluorine-, chlorine-, bromine-, methyl-, trifluoromethyl-, methoxy-, difluoromethoxy-, or trifluoromethoxy-substituted phenyl, phenyl-amino or benzyl.

$R^3$ very particularly preferably represents hydrogen, nitro, cyano, carbamoyl, thiocarbamoyl, fluorine, chlorine, bromine, or represents in each case optionally fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methyl-sulphonyl, ethylsulphonyl, n- or i-propylsulphonyl, methylamino, ethylamino, n- or i-propylamino, dimethylamino, diethylamino, dimethylaminosulphonyl or diethylaminosulphonyl.

$R^4$ very particularly preferably represents hydrogen, nitro, cyano, carbamoyl, thiocarbamoyl, fluorine, chlorine, bromine, or represents in each case optionally fluorine-, chlorine-, methoxy- or ethoxy-substituted methyl, ethyl, n- or i-propyl, methoxy, ethoxy, n- or i-propoxy, methylthio, ethylthio, n- or i-propylthio, methylsulphinyl, ethylsulphinyl, n- or i-propylsulphinyl, methyl-sulphonyl, ethylsulphonyl, n- or i-propylsulphonyl, methylamino, ethylamino, n- or i-propylamino, dimethylamino, diethylamino, dimethylaminosulphonyl or diethylaminosulphonyl.

m very particularly preferably represents the numbers 0, 1 or 2.

$R^5$ very particularly preferably represents in each case optionally fluorine- or chlorine-substituted methyl, ethyl, n- or i-propyl, methylthio, ethylthio, n- or i-propylthio, or optionally also—if m represents 2—together with a second radical $R^5$ represents ethane-1,2-diyl (dimethylene).

$R^6$ very particularly preferably represents hydroxyl.

$R^7$ very particularly preferably represents hydrogen, cyano, fluorine, chlorine, bromine, represents in each case optionally fluorine-, chlorine-, methoxy- or ethoxy-substituted methyl, ethyl, n- or i-propyl, methoxy, ethoxy, n- or i-propoxy, methylthio, ethylthio, n- or i-propylthio, methoxycarbonyl, ethoxy-carbonyl, n- or i-propoxycarbonyl, or represents optionally fluorine-, chlorine- or methyl-substituted cyclopropyl.

$R^8$ very particularly preferably represents hydrogen, represents in each case optionally cyano-, fluorine-, chlorine-, methoxy- or ethoxy-substituted methyl, ethyl, n- or i-propyl, represents in each case optionally fluorine- or chlorine-substituted propenyl, butenyl, propinyl or butinyl, represents in each case optionally fluorine-, chlorine- or methyl-substituted cyclopropyl or cyclopropylmethyl, or represents in each case optionally fluorine-, chlorine-, methyl-, trifluoromethyl-, methoxy-, ethoxy-, difluoromethoxy- or trifluoro-methoxy-substituted phenyl or benzyl.

$R^9$ very particularly preferably represents hydroxyl, formyloxy, represents in each case optionally fluorine-, chlorine-, methoxy- or ethoxy-substituted methoxy, ethoxy, n- or i-propoxy, acetyloxy, propionyloxy, methoxy-carbonyloxy, ethoxycarbonyloxy, methylaminocarbonyloxy, ethylamino-carbonyloxy, methylsulphonyloxy, ethylsulphonyloxy, represents in each case optionally fluorine- or chlorine-substituted propenyloxy, butenyloxy, propinyloxy or butinyloxy, or represents in each case optionally nitro-, cyano-, fluorine-, chlorine-, bromine-, methyl-, trifluoromethyl-, methoxy-, difluoromethoxy- or trifluoromethoxy-substituted phenylmethoxy, benzoyloxy, benzoylmethoxy or phenylsulphonyloxy.

$R^{10}$ very particularly preferably represents hydrogen, cyano, fluorine, chlorine, bromine, or represents in each case optionally fluorine-, chlorine-, methoxy-or ethoxy-substituted methyl, ethyl, n- or i-propyl, acetyl, propionyl, methoxy, ethoxy, n- or i-propoxy, methoxycarbonyl, ethoxycarbonyl, methylthio, ethylthio, n- or i-propylthio.

$R^{11}$ very particularly preferably represents hydrogen, represents in each case optionally fluorine-, chlorine-, methoxy- or ethoxy-substituted methyl, ethyl, n- or i-propyl, or represents optionally fluorine-, chlorine- or methyl-substituted cyclopropyl.

$R^{12}$ very particularly preferably represents hydrogen, represents in each case optionally fluorine-, chlorine-, methoxy- or ethoxy-substituted methyl, ethyl, n- or i-propyl, or represents optionally fluorine-, chlorine- or methyl-substituted cyclopropyl.

$R^{13}$ very particularly preferably represents hydrogen, cyano, fluorine, chlorine, bromine, or represents in each case optionally fluorine-, chlorine- or methoxy-substituted methyl, ethyl, n- or i-propyl, methoxy, ethoxy, n- or i-propoxy, methoxycarbonyl, ethoxycarbonyl, methylthio, ethylthio, n- or i-propylthio, methylsulphinyl, ethylsulphinyl, n- or i-propylsulphinyl, methyl-sulphonyl, ethylsulphonyl, n- or i-propylsulphonyl.

$R^3$ most preferably represents (2)-chloro or (2)-trifluoromethyl.

$R^4$ most preferably represents hydrogen, (4)-chloro or (4)-methylsulphonyl.

Preference according to the invention is given to the compounds of the formula (I) which contain a combination of the meanings listed above as being preferred.

Particular preference according to the invention is given to the compounds of the formula (I) which contain a combination of the meanings listed above as being particularly preferred.

Very particular preference according to the invention is given to the compounds of the formula (I) which contain a combination of the meanings listed above as being very particularly preferred.

Very particular emphasis is given to the compounds of the general formulae (I-1) to (I-6):

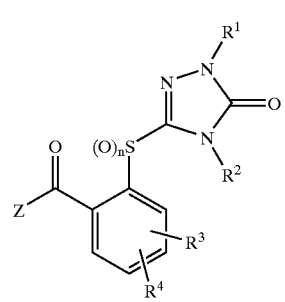
(I-1)

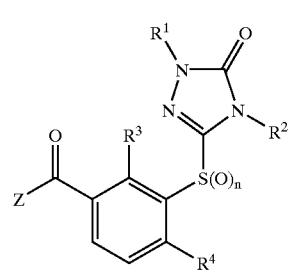
(I-2)

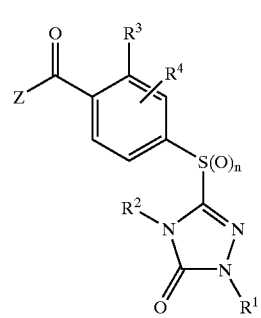
(I-3)

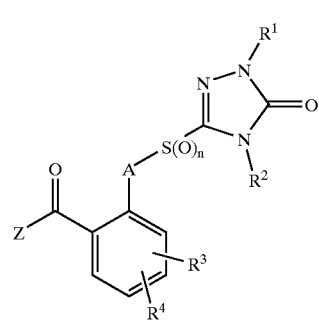
(I-4)

-continued

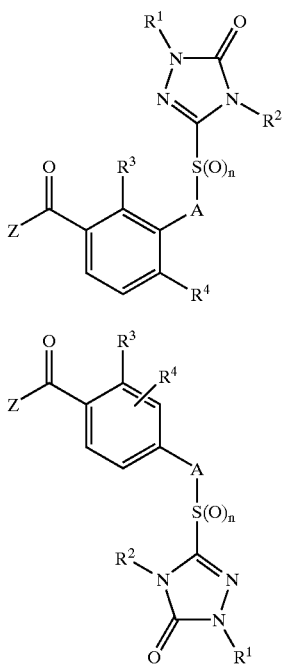

(I-5)

(I-6)

Here, n, A, $R^1$, $R^2$, $R^3$, $R^4$ and Z each have the meanings listed above as being very particularly preferred.

Particular emphasis is given to the compounds of the formulae (I-6) in which represents $Z^1$ and $Z^1$ has the meaning listed above as being very particularly preferred.

Particular emphasis is furthermore given to the compounds of the formulae (I-1) to (I-6) in which Z represents $Z^2$ and $Z^2$ has the meaning listed above as being very particularly preferred.

Particular emphasis is furthermore given to the compounds of the formulae (I-1) to (I-6) in which Z represents $Z^3$ and $Z^3$ has the meaning listed above as being very particularly preferred.

The following tautomeric forms of the compounds of the general formula (I) are feasible:

In the case where $Z=Z^1$, if $R^6$ represents hydroxyl:

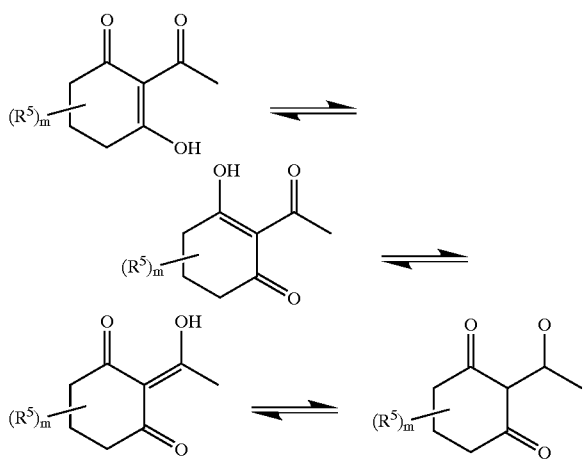

In the case where $Z=Z^2$, if $R^9$ represents hydroxyl:

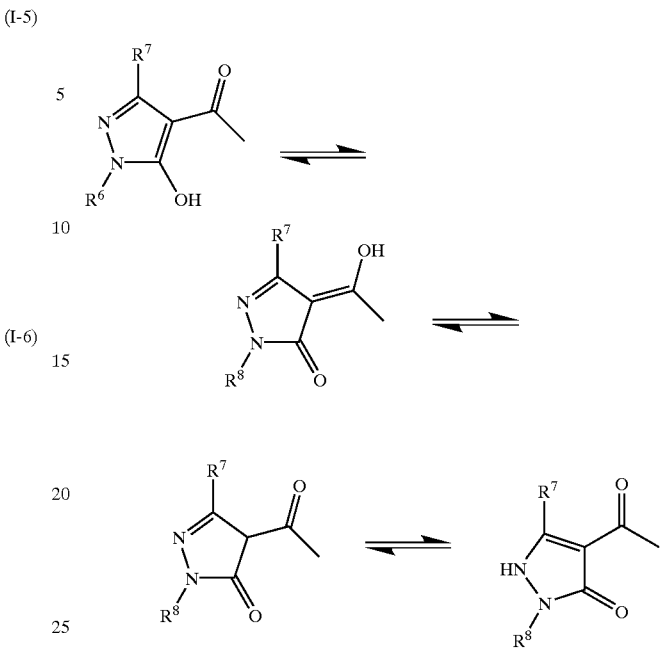

In the case where $Z=Z^4$:

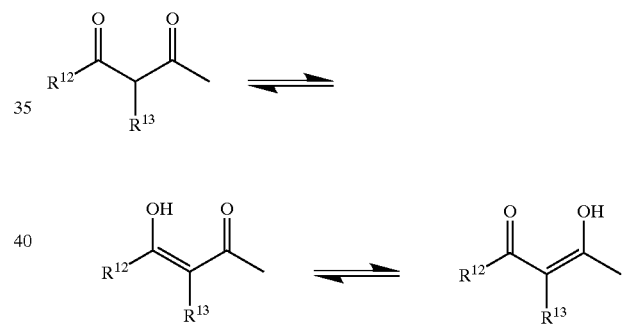

Further tautomeric forms exist, depending on the substituents, and these also form part of the subject-matter of the invention.

The invention also preferably provides, if appropriate, sodium, potassium magnesium, calcium, ammonium, $C_1$–$C_4$-alkyl-ammonium-, di-($C_1$–$C_4$-alkyl)-ammonium, tri-($C_1$–$C_4$-alkyl)-ammonium, tetra-($C_1$–$C_4$-alkyl)-ammonium, tri-($C_1$–$C_4$-alkyl)-sulphonium, $C_5$ or $C_6$-cycloalkyl-ammonium and di-($C_1$–$C_2$-alkyl)-benzyl-ammonium salts of compounds of the formula (1), in which n, A, $R^1$, $R^2$, $R^3$, $R^4$ and Z each have the meanings listed above as being preferred.

The abovementioned general or preferred radical definitions apply both to the end products of the formula (I) and, correspondingly, to the starting materials or intermediates required in each case for the preparation. These radical definitions can be combined with one another as desired, i.e. including combinations between the given preferred ranges.

The novel substituted aryl ketones of the general formula (I) have strong and selective herbicidal activity.

The novel substituted aryl ketones of the general formula (I) are obtained when (a) substituted benzoic acids of the general formula (II)

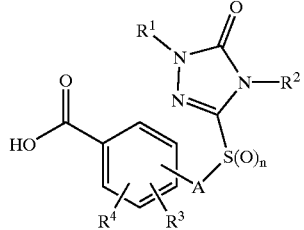

(II)

in which n, A, R$^1$, R$^2$, R$^3$ and R$^4$ are each as defined above

—or reactive derivatives thereof, such as, for example, acid halides, and cyanides or esters— are reacted with compounds of the general formula (III)

<p align="center">Z—H    (III)</p> in which

Z is as defined above, if appropriate in the presence of a dehydrating agent, if appropriate in the presence of one or more reaction auxiliaries and if appropriate in the presence of a diluent, or when (b) halogenoalkyl-aryl ketones of the general formula (IV)

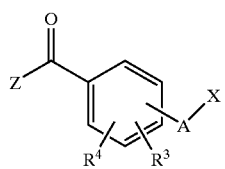

(IV)

in which

A, R$^3$, R$^4$ and Z are each as defined above and

X represents halogen are reacted with compounds of the general formula (V)

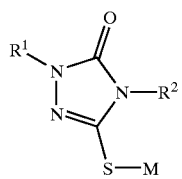

(V)

in which

R$^1$ and R$^2$ are each as defined above and

M represents hydrogen or a metal equivalent, if appropriate in the presence of a reaction auxiliary and if appropriate in the presence of a diluent, or when (c) benzoyl ketones of the general formula (Ia)

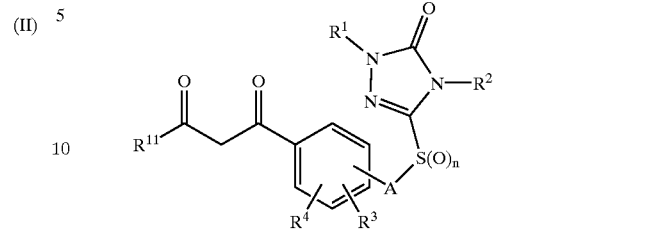

(Ia)

in which n, A, R$^1$, R$^2$, R$^4$ and R$^{11}$ are each as defined above, are reacted with an orthoformic ester or an N,N-dimethylformamide acetal or with a cyanoforic ester or with carbon disulphide and an alkylating agent, and subsequently with hydroxylamine or an acid adduct thereof, if appropriate in the presence of one or more reaction auxiliaries and if appropriate in the presence of one or more diluents, and substitutions, oxidations or reductions within the scope of the definition of the substituents are carried out in a customary manner, if appropriate subsequent to the processes (a), (b) or (c) according to the invention, on the resulting compounds of the general formula (I), and/or the compounds of the general formula (I) are converted in a customary manner into salt-like compounds.

Using, for example, 4-chloro-3-[(1,4-dimethyl-5-oxo-4,5-dihydro-1H-1,2,4-triazol-3-yl)-sulphonyl]-2-fluoro-benzoic acid and 1,3-dimethyl-5-hydroxy-pyrazole as starting materials, the course of the reaction in the process (a) according to the invention can be illustrated by the following equation:

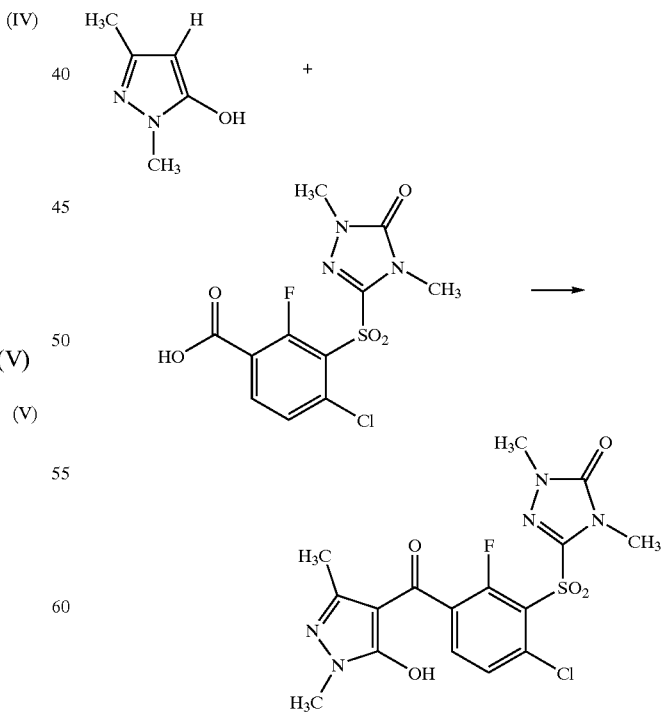

Using for example, 2-(2-chloromethyl-4-trifluoromethyl-benzoyl)-1,3-cyclohexane-1,3-dione and 4-ethyl-2-methyl- 5-mercapto-2,4-dihydro-3H-1,2,4-triazol-3-one as starting materials, the course of the reaction in the process (b) according to the invention can be illustrated by the following equation:

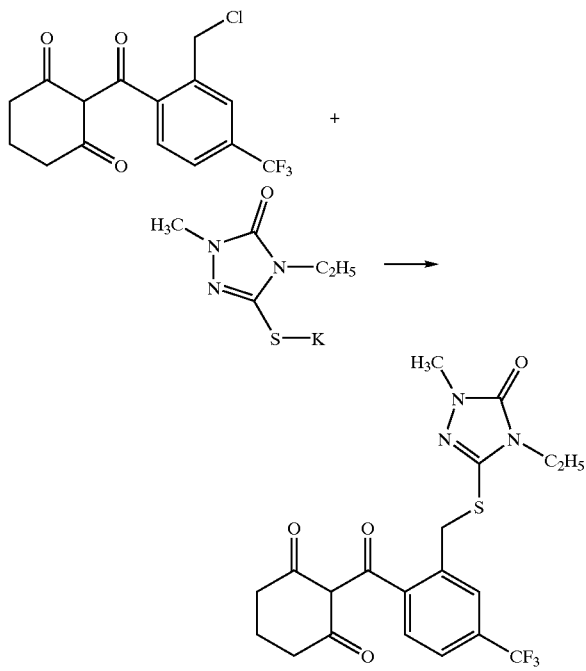

Using, for example 1-[2-chloro-4-[(4,5-dihydro-1,4-dimethyl-5-oxo-1H-1,2,4-triazol-3-yl)-sulphanyl]-phenyl]-3-cyclopropyl-1,3-propanedione, ethyl cyanoformate and hydroxylamine as starting materials, the course of the reaction in the process (c) according to the invention can be illustrated by the following equation:

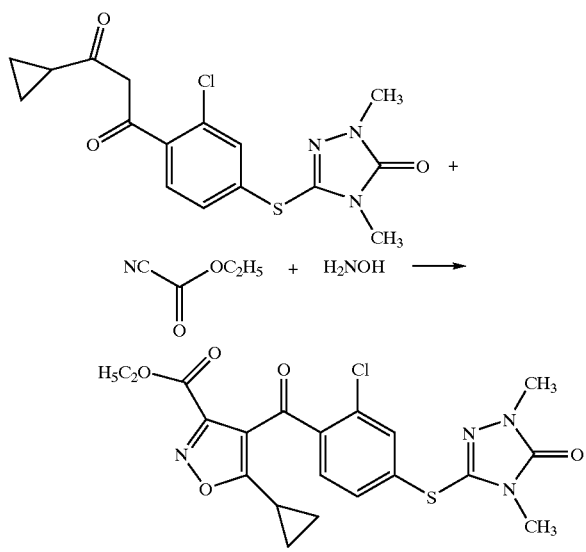

The formula (II) provides a general definition of the substituted benzoic acids to be used as starting materials in the process (a) according to the invention for preparing compounds of the general formula (I). In the general formula (II), n, A, $R^1$, $R^2$, $R^3$ and $R^4$ each preferably have those meanings which have already been mentioned above, in connection with the description of the compounds of the general formula (I) according to the invention, as being preferred, particularly preferred or very particularly preferred for n, A, $R^1$, $R^2$, $R^3$ and $R^4$.

The starting materials of the general formula (II) are known and/or can be prepared by processes known per se (cf. WO-A-96/35680).

The substituted benzoic acids of the general formula (II) are obtained when substituted benzoic acid derivatives of the general formula (VI)

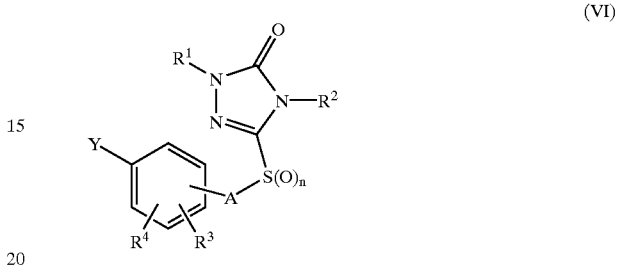

in which n, A, $R^1$, $R^2$, $R^3$ and $R^4$ are each as defined above and

Y represents cyano or alkoxycarbonyl (in particular methoxycarbonyl, ethoxy-carbonyl, n- or i-propoxycarbonyl, n-, i-, s- or t-butoxycarbonyl)

are reacted with water, if appropriate in the presence of a hydrolysis auxiliary, Such as, for example, hydrobromic acid, sulphuric acid or aqueous sodium hydroxide solution, and if appropriate in the presence of an organic solvent, such as, for example, dioxane, at temperatures between 50° C. and 120° C. (cf. the Preparation Examples).

The precursors of the general formula (VI) are known and/or can be prepared by processes known per se (cf. WO-A-96/35680, Preparation Examples).

The formula (III) provides a general definition of the compounds further to be used as starting materials in the process (a) according to the invention for preparing compounds of the general formula (I). In the general formula (III), Z preferably has that meaning which has already been mentioned above, in connection with the description of the compounds of the general formula (I) according to the invention, as being preferred, particularly preferred or very particularly preferred for Z.

The starting materials of the general formula (III) are known and/or can be prepared by processes known per se.

The formula (IV) provides a general definition of the halogenoalkyl-aryl ketones to be used as starting materials in the process (b) according to the invention for preparing compounds of the general formula (I). In the general formula (IV), A, $R^3$, $R^4$ and Z each preferably have those meanings which have already been mentioned above, in connection with the description of the compounds of the general formula (I) according to the invention, as being preferred, particularly preferred or very particularly preferred for A, $R^3$, $R^4$ and Z; X preferably represents fluorine, chlorine, bromine or iodine, in particular chlorine or bromine.

The starting materials of the general formula (IV) are known and/or can be prepared by processes known per se (cf. EP-A-90 369, EP-A-93 488, EP-A-399 732, EP-A-480 641, EP-A-609 798, EP-A-763 524, DE-A-2 126 720, WO-A-93/03722, WO-A-97/38977, U.S. Pat. Nos. 3,978, 127, 4,837,333).

The formula (V) provides a general definition of the compounds further to be used as starting materials in the process (b) according to the invention for preparing compounds of the general formula (I). In the general formula (V), $R^1$ and $R^2$ each preferably have those meanings which have already been mentioned above, in connection with the description of the compounds of the general formula (I) according to the invention, as being preferred, particularly preferred or very particularly preferred for $R^1$ and $R^2$; M preferably represents hydrogen or represents a lithium, sodium, potassium, rubidium, caesium, magnesium or calcium equivalent, in particular hydrogen, sodium or potassium.

The starting materials of the general formula (V) are known and/or can be prepared by processes known per se (cf. J. Med. Chem. 35 (1992), 2573–2581;, U.S. Pat. No. 3,767,666).

The formula (Ia) provides a general definition of the benzoyl ketones to be used as starting materials in the process (c) according, to the invention for preparing compounds of the general formula (I). In the general formula (Ia), n, A, $R^1$, $R^2$, $R^3$, $R^4$ and $R^{11}$ each preferably have those meanings which have already been mentioned above, in connection with the description of the compounds of the general formula (I) according to the invention, as being preferred, particularly preferred or very particularly preferred for n, A, $R^1$, $R^2$, $R^3$, $R^4$ and $R^{11}$.

The starting materials of the general formula (Ia) are novel compounds according to the invention; they can be prepared by the process (a) or (b) according to the The process (a) according to the invention for preparing the novel substituted aryl ketones of the general formula (I) is preferably carried out using a dehydrating agent. Suitable dehydrating agents are the customary chemicals suitable for binding water.

Examples of these which may be mentioned are dicyclohexylcarbodiimide and carbonyldiimidazole.

A particularly suitable dehydrating agent which may be mentioned is dicyclohexyl-carbodiimide.

The process (a) according to the invention for preparing the novel substituted aryl ketones of the general formula (I) is, if appropriate, carried out using one or more reaction auxiliaries.

Examples of these which may be mentioned are sodium cyanide, potassium cyanide, acetone cyanohydrin, 2-cyano-2-(trimethylsilyloxy)-propane and trimethylsilyl-cyanide.

A particularly suitable further reaction auxiliary which may be mentioned is trimethylsilyl cyanide.

The process (a) according to the invention for preparing the novel substituted aryl ketones of the general formula (I) is, if appropriate, carried out using a further reaction auxiliary. Suitable further reaction auxiliaries for the process according to the invention are, in general, basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-di methyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]-octane (DABCO), 1,5-diazabicyclo[4.3.0]-non-5-ene (DBN), or 1,8-diazabicyclo[5.4.0]-undec-7-ene (DBU).

The process (c) according to the invention for preparing the compounds of the formula (I) is, if appropriate, carried out using orthoforic esters or N,N-dimethyl-formamide acetals. These compounds preferably contain alkyl groups having 1 to 4 carbon atoms, in particular methyl or ethyl. Examples which may be mentioned are trimethyl orthoformate, triethyl orthoformate, N,N-dimethyl-formamide dimethyl acetal and N,N-dimethyl-formamide diethyl acetal.

The process (c) according to the invention for preparing compounds of the formula (I) is, if appropriate, carried out using cyanoformic esters. These compounds preferably contain alkyl groups having 1 to 4 carbon atoms, in particular methyl or ethyl. Examples which may be mentioned are methyl cyanoformate and ethyl cyano formate.

The process (c) according to the invention for preparing compounds of the formula (I) is, if appropriate, carried out using (carbondisulphide and) alkylating agents. These compounds preferably contain alkyl groups having 1 to 4 carbon atoms, in particular methyl or ethyl. Examples which may be mentioned are methyl chloride, methyl bromide, methyl iodide, dimethyl sulphate, ethyl chloride, ethyl bromide, ethyl iodide and diethyl sulphate.

The process (c) according to the invention for preparing compounds of the formula (I) is carried out using hydroxylamine or an acid adduct thereof. Hydroxylamine hydrochloride may be mentioned as preferred acid adduct.

The processes (b) and (c) according to the invention for preparing the compounds of the general formula (I) are preferably carried out using a reaction auxiliary. Suitable reaction auxiliaries for the processes (b) and (c) according to the invention are, in general, the customary inorganic or organic bases or acid acceptors. These preferably include alkali metal or alkaline earth metal acetates, amides, carbonates, bi-carbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzyl-amine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethyl-aminopyridine, N-methyl-piperidine, 1,4-diazabicyclo[2.2.2]-octane (DABCO), 1,5-diazabicyclo[4.3.0]-non-5-ene (DBN) or 1,8-diazabicyclo[5.4.0]-undec-7-ene (DBU).

The processes according to the invention for preparing the compounds of the general formula (I) are preferably carried out using diluents. Suitable diluents for carrying out the processes (a), (b) and (c) according to the invention are especially inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or butyronitrile; amides, such as N,N-dimethylformamide, N,N-dimethylacetamide, N-methyl-formanilide, N-methylpyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether.

When carrying out the processes (a), (b) and (c) according to the invention, the reaction temperatures can be varied within a relatively wide range. In general, the processes are carried out at temperatures between 0° C. and 150° C., preferably between 10° C. and 120° C.

The processes (a), (b) and (c) according to the invention are generally carried out under atmospheric pressure. However, it is also possible to carry out the processes according to the invention under elevated or reduced pressure—in general between 0.1 bar and 10 bar.

For carrying out the processes (a), (b) and (c) according to the invention, the starting materials are generally employed in approximately equimolar amounts. However, it is also possible to use a relatively large excess of one of the components. The reaction is generally carried out in a suitable diluent and the reaction mixture is generally stirred at the required temperature for several hours. Work-up is carried out by customary methods (cf. the Preparation Examples).

The active compounds according to the invention can be used as defoliants, desiccants, haulm killers and, especially, as weed killers. Weeds in the broadest sense are understood to mean all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Abutilon, Amaranthus, Ambrosia, Atioda, Anthemis, Aphanes, Atriplex, Bellis, Bidens, Capsella, Carduus, Cassia, Centaurca, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindemia, Matricaria, Mentha, Mercurialis, Mullugo, Myosotis, Papaver, Pharbitis, Plantago, Polygonum, Portulaca, Ranunculus, Raphalus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.

Dicotyledolous crops of the genera: Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia.

Monocotyledonous weeds of the genera: Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.

Monocotyledonous crops of the genera: Allium, Ananas Asparagus, Avena, Hordeum, Oryza, Panicum, Saccharum, Secale, Sorghum, Triticale, Triticum, Zea.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and areas with and without tree plantings. Similarly, the compounds can be employed for controlling weeds in perennial crops, for example forests, decorative tree plantings, orchards, vineyards, citrus groves, nut orchards, banana plantations, coffee plantations, tea plantations, rubber plantations, oil palm plantations, cocoa plantations, soft fruit plantings and hop fields, on lawns, turf and pastureland, and for the selective control of weeds in annual crops.

The compounds of the formula (I) according to the invention are suitable, in particular, for the selective control of monocotyledonous and dicotyledonous weeds in monocotyledonous crops, both by the preemergence and by the post-emergence method.

At certain concentrations or application rates, the active compounds according to the invention can also be employed for controlling animal pests and fungal or bacterial plant diseases. If appropriate, they can also be used as intermediates or precursors for the synthesis of other active compounds.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by action on their environment, habitat or storage area according to customary treatment methods, for example by dipping, spraying, evaporating, atomizing broadcasting, brushing-on and, in the case of propagation material, in particular in the case of seeds, furthermore by one- or multi-layer coating.

The active compounds can be converted into the customary formulations, such as solutions, emulsions, wettable powders, suspensions, powders, dusts, pastes, soluble powders, granules, suspo-emulsion concentrates, natural and synthetic substances impregnated with active compound, and microencapsulations in polymeric substances.

These formulations are produced in a known manner, for example by mixing the active compounds with extenders, that is to say liquid solvents and/or solid carriers, optionally with the use of surfactants, that is to say emulsifiers and/or dispersants and/or foam-formers.

If the extender used is water, it is also possible to use, for example, organic solvents as auxiliary solvents. Liquid solvents which are mainly suitable are: aromatics, such as xylene, toluene or alkylnaphthalenes, chlorinated aromatics and chlorinated aliphatic hydrocarbons, Such as chlorobenzenes, chloroethylenes or methylene chloride, aliphatic hydrocarbons, such as cyclohexane or paraffins, for example petroleum fractions, mineral and vegetable oils, alcohols, such as butanol or glycol, and also their ethers and esters, ketones, such as acetone, methyl ethyl ketone, methyl isobutyl ketone or cyclohexanone, strongly polar solvents, such as dimethyl-formamide and dimethyl sulphoxide, and water.

Suitable solid carriers are: for example ammonium salts and ground natural minerals, such as kaolins, clays, talc, chalk, quartz, attapulgite, montmorillonite or diato-maceous earth, and ground synthetic minerals, such as finely divided silica, alumina and silicates; suitable solid carriers for granules are: for example crushed and fractionated natural rocks, such as calcite, marble, pumice, sepiolite, dolomite and synthetic granules of inorganic and organic meals, and granules of organic material, such as sawdust, coconut shells, maize cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates; suitable dispersants are: for example lignosulphite waste liquors and methylcellulose.

Tackifiers, such as carboxymethylcellulose, natural and synthetic polymers in the form of powders, granules or latices, such as gum arabic, polyvinyl alcohol and polyvinyl acetate, and also natural phospholipids, such as cephalins and lecithins, and synthetic phospholipids can be used in the formulations. Other possible additives are mineral and vegetable oils. It is possible to use colorants, such as inorganic pigments, for example iron oxide, titanium oxide, Prussian blue, and organic dyestuffs, such as alizarin dyestuffs, azo dyestuffs and metal phthalocyanine dyestuffs, and trace nutrients, such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in their formulations, can also be used as mixtures with known herbicides and/or substances which improve the compatibility with crop plants ("safeners"), finished formulations or tank mixes being possible. Also possible are mixtures with weed-killers comprising one or more known herbicides and a safener.

Possible components for the mixtures are known herbicides, for example acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazon, benzfendizone, benzobicyclon, benzofenap, benzoylprop(-ethyl), bialaphos, bifenox, bispyribac-(-sodium), bromobutide, bromofenoxim, bromoxynil, butachlor, butafenacil, butroxydim, butylate, cafenstrole, caloxydim, carbetamide, carfentrazone(-ethyl), chlomethoxyfen, chloramben, chloridazon, chlorimuron(-ethyl), chlomitrofen, chlorsulfuron, chlortoluron, cinidon(-ethyl), cinmethylin, cinosulfuron, clefoxydim, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, diallate, dicnamba, diclofop(-methyl), diclosulam, diethatyl(-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymron, epropodan, EPTC, esprocarb, ethalfluralin, ethametsulfuron(-methyl), ethofumesate, ethoxyfen, ethoxysulfuron, etobenzanid, fenoxaprop(-P-ethyl), fentrazamide, flamprop(-isopropyl), flamprop(-isopropyl-L), flamprop(-methyl), flazasulfuron, florasulam, fluazifop(-P-butyl), fluazolate, flucarbazone(-sodium), flufenacet, flumetsulam, flumiclorac(-pentyl), flumioxazin, flumipropyn, flumetsulam, fluometuron, fluorineochiloridone, fluoroglycofen(-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), lyphosate(-isopropylammonium), halosafeni, haloxyfop(-ethoxyethyl), haloxyfop(-P-methyl), hexazinone, imazamethabenz(-methyl), imazamethapyr, imazamox, imazapic, imazapyr, imazaquin, imazethapyr, imazosulfuron, iodosulfuron(-methyl-, -sodium), ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, methabenzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pendralin, pentoxazone, pethoxamid, phenmedipham, picolinafen, piperophos, pretilachlor, primisulfuron(-methyl), procarbazone(-sodium), prometryn, propachlor, propanil, propaquizafop, propisochlor, propyzamide, prosulfocarb, prosulfulron, pyraflufen-(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, qulinoclamine, quizalofop(-P-ethyl), quizalofop(-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, triallate, triasulfuron, tribenuron(-methyl), triclopyr, tridiphane, trifluralin and triflusulfuron, tritosulfuron.

A mixture with other known active compounds, such as fungicides, insecticides, acaricides, nematicides, bird repellents, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in a customary manner, for example by watering, spraying, atomizing or broadcasting.

The active compounds according to the invention can be applied both before and after emergence of the plants. They can also be incorporated into the soil before sowing.

The amount of active compound used can vary within a relatively wide range. It depends essentially on the nature of the desired effect. In general, the amounts used are between 1 g and 10 kg of active compound per hectare of soil surface, preferably between 5 g and 5 kg per ha.

The preparation and the use of the active compounds according to the invention is illustrated by the examples below.

Preparation Examples

EXAMPLE 1

(Process (a))

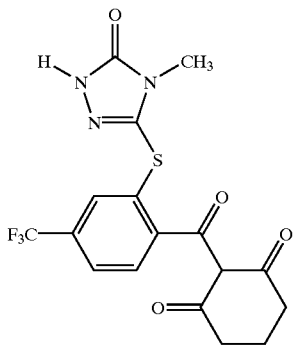

A mixture of 0.80 g (2.5 mmol) of 2-[(4-methyl-5-oxo-4,5-dihydro-1H-1,2,4-triazol-3-yl)-sulphanyl]-4-trifluoromethyl-benzoic acid, 0.28 g (2.5 mmol) of 1,3-cyclohexanedione and 0.63 g (3.1 mmol) of N,N'-dicyclohexylcarbodiimide is stirred at room temperature (approximately 20° C.) for 48 hours. 0.7 ml (5 mmol) of triethylamine and a drop of trimethylsilyl cyanide are then added, and the mixture is stirred for a further 24 hours. The mixture is then concentrated under water pump vacuum and the residue is stirred with 10% strength aqueous sodium carbonate solution. The mixture is then filtered and the filtrate is washed twice with diethyl ether, acidified with 2N hydrochloric acid and extracted with dichloromethane. The organic phase is dried over magnesium sulphate and the solvent is removed under reduced pressure, giving 0.7 g (68% of theory) of 2-[2-[(4-methyl-5-oxo-4,5-dihydro-1H-1,2,4-triazol-3-yl)-sulphanyl]-4-trifluoromethyl-benzoyl]-1,3-cyclohexanedione as an oil (log P=2.00).

EXAMPLE 2

(Process (a))

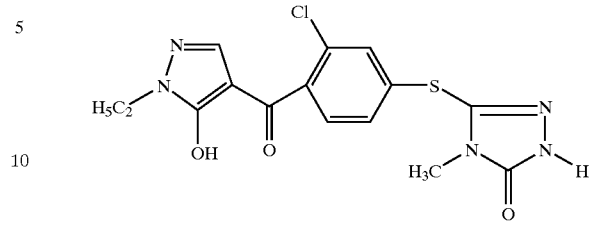

A mixture of 1.45 g (5 mmol) of 2-chloro-4-[(4-methyl-5-oxo-4,5-dihydro-1H-1,2,4-triazol-3-yl)-sulphanyl]-benzoic acid, 0.70 g (6 mmol) of 1-ethyl-5-hydroxy-pyrazole, 1.3 g (6 mmol) of dicyclohexylcarbodiimide and 100 ml of methylene chloride is stirred at room temperature (approximately 20° C.) for 16 hours. The mixture is then filtered and the filtrate is washed with water, dried with sodium sulphate and filtered. The filtrated is concentrated and the residue is taken up in 50 ml of dioxane and heated under reflux with 1.4 g (10 mmol) of potassium carbonate and 3 drops of trimethylsilyl cyanide for 60 minutes. The mixture is then taken up in 150 ml of water and shaken twice with methylene chloride. 100 ml of methylene chloride are then added to the aqueous phase, and the mixture is acidified with stirring with hydrochloric acid. The organic phase is separated off, dried with sodium sulphate and filtered. The filtrate is concentrated under water pump vacuum, the residue is digested with diethyl ether and the resulting crystalline product is isolated by filtration with suction.

This gives 0.90 g (47% of theory) of 5-[3-chloro-[4-(1-ethyl-5-hydroxy-1H-pyrazol-4-yl]-carbonyl]-phenylsulphanyl]-4-methyl-2,4-dihydro-3H-1,2,4-triazol-3-one of melting point 216° C.

Analogously to Examples 1 and 2, and in accordance with the general description of the preparation processes according to the invention, it is also possible to prepare, for example, the compounds of the general formula (I) listed in Table 1 below.

TABLE 1

(I)

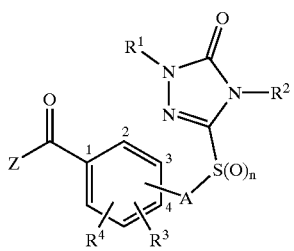

Examples of compounds of the formula (I)

| Ex. No. | n | (position) A | $R^1$ | $R^2$ | (position) $R^3$ | (position) $R^4$ | Z |
|---|---|---|---|---|---|---|---|
| 3 | 0 | (4) — | $CH_3$ | $CH_3$ | (2) Cl | — | 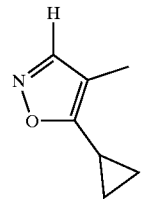 |

TABLE 1-continued

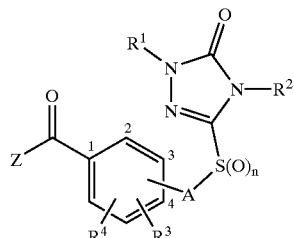

Examples of compounds of the formula (I)

| Ex. No. | n | (position) A | $R^1$ | $R^2$ | (position) $R^3$ | (position) $R^4$ | Z | Physical data |
|---|---|---|---|---|---|---|---|---|
| 4 | 0 | (4) | H | $CH_3$ | (2) Cl | — | 2-methyl-cyclohexane-1,3-dione | m.p.: 98° C. |
| 5 | 0 | (4) | $CH_3$ | $CH_3$ | (2) Cl | — | 1-ethyl-4-methyl-5-hydroxypyrazole | m.p.: 137° C. |
| 6 | 0 | (4) | $CH_3$ | $CH_3$ | (2) Cl | — | 2-methyl-cyclohexane-1,3-dione | logP = 2.08[a] |
| 7 | 2 | (4) | H | $CH_3$ | (2) Cl | — | 1-ethyl-4-methyl-5-hydroxypyrazole | m.p.: 213° C. |
| 8 | 0 | (4) | $CH_3$ | $CH_3$ | (2) Cl | — | 1,4-dimethyl-5-hydroxypyrazole | m.p.: 140° C. |
| 9 | 0 | (4) | $CH_3$ | $CH_3$ | (2) Cl | — | 1,3,4-trimethyl-5-hydroxypyrazole | logP = 1.34[a] |
| 10 | 2 | (4) | $CH_3$ | $CH_3$ | (2) Cl | — | 1-ethyl-4-methyl-5-hydroxypyrazole | m.p.: 164° C. |

TABLE 1-continued

Examples of compounds of the formula (I)

| Ex. No. | n | (position) A | R¹ | R² | (position) R³ | (position) R⁴ | Z | Physical data |
|---|---|---|---|---|---|---|---|---|
| 11 | 2 | (4) — | CH₃ | CH₃ | (2) Cl | — | 1-methyl-5-hydroxy-4-methylpyrazol-3-yl (N-CH₃, C4-CH₃, C5-OH, C3-H) | m.p.: 187° C. |
| 12 | 2 | (4) — | CH₃ | CH₃ | (2) Cl | — | 1,3-dimethyl-5-hydroxy-4-methylpyrazol-... (N-CH₃, C3-CH₃, C4-CH₃, C5-OH) | m.p.: 225° C. |
| 13 | 2 | (4) — | CH₃ | CH₃ | (2) Cl | — | 2-methyl-1,3-cyclohexanedion-... | log P = 2.09[a] |
| 14 | 2 | (4) — | H | CH₃ | (2) Cl | — | 2-methyl-1,3-cyclohexanedion-... | log P = 1.88[a] |
| 15 | 0 | (2) — | CH₃ | CH₃ | (4) CF₃ | — | 2-methyl-1,3-cyclohexanedion-... | |
| 16 | 0 | (2) CH₂ | CH₃ | CH₃ | (4) CF₃ | — | 2-methyl-1,3-cyclohexanedion-... | log P = 2.41[a] |
| 17 | 0 | (2) CH₂ | CH₃ | CH₃ | (4) CF₃ | — | 1-ethyl-5-hydroxy-4-methylpyrazol-3-yl (N-C₂H₅, C4-CH₃, C5-OH, C3-H) | log P = 2.16[a] |

TABLE 1-continued

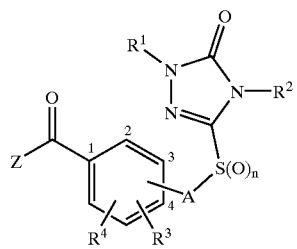

Examples of compounds of the formula (I)

| Ex. No. | n | (position) A | R¹ | R² | (position) R³ | (position) R⁴ | Z | Physical data |
|---|---|---|---|---|---|---|---|---|
| 18 | 0 | (3) CH$_2$ | H | CH$_3$ | (2) Cl | (4) Cl | 2-methyl-cyclohexane-1,3-dione | m.p.: 187° C. |
| 19 | 0 | (3) CH$_2$ | H | CH$_3$ | (2) Cl | (4) Cl | 1-ethyl-4-methyl-5-hydroxypyrazole | logP = 1.61[a)] |
| 20 | 0 | (3) CH$_2$ | CH$_3$ | CH$_3$ | (2) Cl | (4) Cl | 2-methyl-cyclohexane-1,3-dione | logP = 2.24[a)] |
| 21 | 0 | (3) CH$_2$ | CH$_3$ | CH$_3$ | (2) Cl | (4) Cl | 1-ethyl-4-methyl-5-hydroxypyrazole | logP = 1.82[a)] |
| 22 | 1 | (3) CH$_2$ | H | CH$_3$ | (2) Cl | (4) Cl | 2-methyl-cyclohexane-1,3-dione | logP = 1.60[a)] |
| 23 | 2 | (3) CH$_2$ | CH$_3$ | CH$_3$ | (2) Cl | (4) Cl | 2-methyl-cyclohexane-1,3-dione | logP = 2.09[a)] |
| 24 | 2 | (3) CH$_2$ | CH$_3$ | CH$_3$ | (2) Cl | (4) Cl | 1-ethyl-4-methyl-5-hydroxypyrazole | logP = 1.62[a)] |

TABLE 1-continued

Examples of compounds of the formula (I)

| Ex. No. | n | (position) A | R¹ | R² | (position) R³ | (position) R⁴ | Z | Physical data |
|---|---|---|---|---|---|---|---|---|
| 25 | 2 | (3) CH₂ | H | CH₃ | (2) Cl | (4) Cl | 2-methylcyclohexane-1,3-dione | logP = 1.87[a] |
| 26 | 2 | (3) CH₂ | H | CH₃ | (2) Cl | (4) Cl | 1-ethyl-5-hydroxy-4-methylpyrazole | logP = 1.45[a] |
| 27 | 1 | (3) CH₂ | CH₃ | CH₃ | (2) Cl | (4) Cl | 1-ethyl-5-hydroxy-4-methylpyrazole | logP = 1.42[a] |
| 28 | 1 | (3) CH₂ | H | CH₃ | (2) Cl | (4) Cl | 2-methylcyclohexane-1,3-dione | logP = 1.61[a] |
| 29 | 0 | (3) CH₂ | H | CH₃ | (2) Cl | (4) SO₂CH₃ | 2-methylcyclohexane-1,3-dione | |
| 30 | 1 | (3) CH₂ | H | CH₃ | (2) Cl | (4) SO₂CH₃ | 2-methylcyclohexane-1,3-dione | |
| 31 | 2 | (3) CH₂ | H | CH₃ | (2) Cl | (4) SO₂CH₃ | 2-methylcyclohexane-1,3-dione | |

TABLE 1-continued

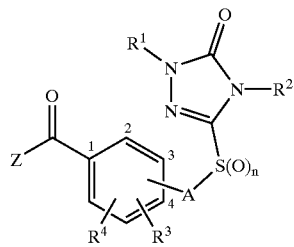

Examples of compounds of the formula (I)

| Ex. No. | n | (position) A | R¹ | R² | (position) R³ | (position) R⁴ | Z | Physical data |
|---|---|---|---|---|---|---|---|---|
| 32 | 0 | (3) CH₂ | CH₃ | CH₃ | (2) Cl | (4) SO₂CH₃ | 2-methylcyclohexane-1,3-dione | |
| 33 | 1 | (3) CH₂ | CH₃ | CH₃ | (2) Cl | (4) SO₂CH₃ | 2-methylcyclohexane-1,3-dione | |
| 34 | 2 | (3) CH₂ | CH₃ | CH₃ | (2) Cl | (4) SO₂CH₃ | 2-methylcyclohexane-1,3-dione | |
| 35 | 0 | (3) CH₂ | C₂H₅ | CH₃ | (2) Cl | (4) SO₂CH₃ | 1-ethyl-4-methyl-5-hydroxypyrazole | |
| 36 | 1 | (3) CH₂ | C₂H₅ | CH₃ | (2) Cl | (4) SO₂CH₃ | 1-ethyl-4-methyl-5-hydroxypyrazole | |
| 37 | 2 | (3) CH₂ | C₂H₅ | CH₃ | (2) Cl | (4) SO₂CH₃ | 1-ethyl-4-methyl-5-hydroxypyrazole | |
| 38 | 0 | (3) CH₂ | H | CH₃ | (2) Cl | (4) SO₂CH₃ | 1-ethyl-4-methyl-5-hydroxypyrazole | |

TABLE 1-continued
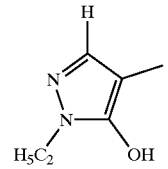
Examples of compounds of the formula (I)
| Ex. No. | n | (position) A | R¹ | R² | (position) R³ | (position) R⁴ | Z | Physical data |
|---|---|---|---|---|---|---|---|---|
| 39 | 1 | (3) CH₂ | H | CH₃ | (2) Cl | (4) SO₂CH₃ | 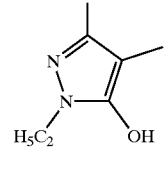 | |
| 40 | 2 | (3) CH₂ | H | CH₃ | (2) Cl | (4) SO₂CH₃ | 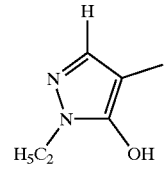 | |
| 41 | 0 | (3) CH₂ | CH₃ | CH₃ | (2) Cl | (4) SO₂CH₃ | 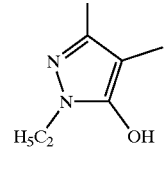 | |
| 42 | 1 | (3) CH₂ | CH₃ | CH₃ | (2) Cl | (4) SO₂CH₃ | | |
| 43 | 2 | (3) CH₂ | CH₃ | CH₃ | (2) Cl | (4) SO₂CH₃ | 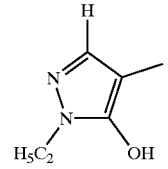 | |
| 44 | 0 | (3) CH₂ | C₂H₅ | CH₃ | (2) Cl | (4) SO₂CH₃ | 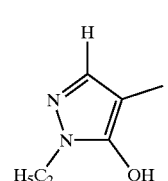 | |

TABLE 1-continued

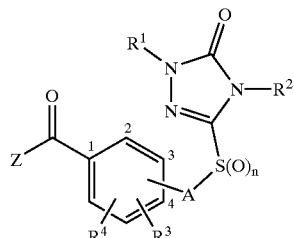

Examples of compounds of the formula (I)

| Ex. No. | n | (position) A | R¹ | R² | (position) R³ | (position) R⁴ | Z | Physical data |
|---|---|---|---|---|---|---|---|---|
| 45 | 1 | (3) CH₂ | C₂H₅ | CH₃ | (2) Cl | (4) SO₂CH₃ | 4-methyl-5-hydroxy-1-ethylpyrazol-3-yl | |
| 46 | 2 | (3) CH₂ | C₂H₅ | CH₃ | (2) Cl | (4) SO₂CH₃ | 4-methyl-5-hydroxy-1-ethylpyrazol-3-yl | |
| 47 | 0 | (4) — | C₂H₅ | CH₃ | (2) Cl | — | 2-methyl-1,3-cyclohexanedion-yl | logP = 2.34[a] |
| 48 | 0 | (4) — | C₂H₅ | CH₃ | (2) Cl | — | 4-methyl-5-hydroxy-1-ethylpyrazol-3-yl | m.p.: 150° C. |
| 49 | 0 | (4) — | n-C₃H₇ | CH₃ | (2) Cl | — | 2-methyl-1,3-cyclohexanedion-yl | logP = 2.63[a] |
| 50 | 0 | (4) — | n-C₃H₇ | CH₃ | (2) Cl | — | 4-methyl-5-hydroxy-1-ethylpyrazol-3-yl | logP = 2.14[a] |
| 51 | 0 | (4) — | H₂C=CH-CH₂- (allyl) | CH₃ | (2) Cl | — | 2-methyl-1,3-cyclohexanedion-yl | logP = 2.47[a] |

TABLE 1-continued

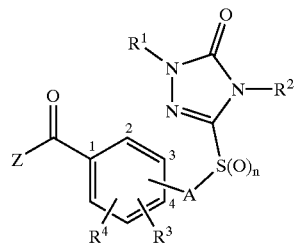

Examples of compounds of the formula (I)

| Ex. No. | n | (position) A | R¹ | R² | (position) R³ | (position) R⁴ | Z | Physical data |
|---|---|---|---|---|---|---|---|---|
| 52 | 0 | (4) — | H₂C=CH–CH₂– | CH₃ | (2) Cl | — | 4-methyl-1-ethyl-5-hydroxypyrazol-3-yl | logP = 2.00[a] |
| 53 | 0 | (4) — | HC≡C–CH₂– | CH₃ | (2) Cl | — | 2-methyl-1,3-cyclohexanedion-2-yl | logP = 2.37[a] |
| 54 | 0 | (4) — | HC≡C–CH₂– | CH₃ | (2) Cl | — | 4-methyl-1-ethyl-5-hydroxypyrazol-3-yl | logP = 1.90[a] |
| 55 | 0 | (4) — | cyclopropylmethyl | CH₃ | (2) Cl | — | 2-methyl-1,3-cyclohexanedion-2-yl | logP = 2.72[a] |
| 56 | 0 | (4) — | cyclopropylmethyl | CH₃ | (2) Cl | — | 4-methyl-1-ethyl-5-hydroxypyrazol-3-yl | logP = 2.22[a] |
| 57 | 0 | (4) — | benzyl | CH₃ | (2) Cl | — | 2-methyl-1,3-cyclohexanedion-2-yl | logP = 3.04[a] |
| 58 | 0 | (4) — | benzyl | CH₃ | (2) Cl | — | 4-methyl-1-ethyl-5-hydroxypyrazol-3-yl | logP = 2.55[a] |

TABLE 1-continued

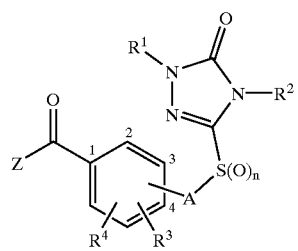

Examples of compounds of the formula (I)

| Ex. No. | n | (position) A | R¹ | R² | (position) R³ | (position) R⁴ | Z | Physical data |
|---|---|---|---|---|---|---|---|---|
| 59 | 0 | (4) | H | cyclopropyl | (2) Cl | — | 2-methylcyclohexane-1,3-dione | |
| 60 | 0 | (4) | H | cyclopropyl | (2) Cl | — | 1-ethyl-5-hydroxy-4-methylpyrazole | |
| 61 | 0 | (4) | H | OC₂H₅ | (2) Cl | — | 2-methylcyclohexane-1,3-dione | |
| 62 | 0 | (4) | H | OC₂H₅ | (2) Cl | — | 1-ethyl-5-hydroxy-4-methylpyrazole | |
| 63 | 0 | (4) | CH₃ | cyclopropyl | (2) Cl | — | 2-methylcyclohexane-1,3-dione | |
| 64 | 0 | (4) | CH₃ | cyclopropyl | (2) Cl | — | 1-ethyl-5-hydroxy-4-methylpyrazole | |
| 65 | 0 | (4) | CH₃ | OC₂H₅ | (2) Cl | — | 2-methylcyclohexane-1,3-dione | |

TABLE 1-continued

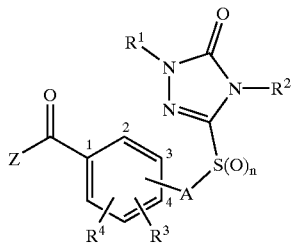

Examples of compounds of the formula (I)

| Ex. No. | n | (position) A | R¹ | R² | (position) R³ | (position) R⁴ | Z | Physical data |
|---|---|---|---|---|---|---|---|---|
| 66 | 0 | (4) — | CH₃ | OC₂H₅ | (2) Cl | — | pyrazole structure (H, CH₃, N-N, H₅C₂, OH) | |
| 67 | 0 | (4) — | CH₃ | CH₃ | (2) Cl | — | cyclopropyl-C(O)-CH(CN)-CH₃ | |
| 68 | 2 | (2) — | CH₃ | CH₃ | (4) CF₃ | — | 2-methyl-cyclohexane-1,3-dione | logP = 1.85ᵃ⁾ |
| 69 | 2 | (2) — | CH₃ | CH₃ | (4) CF₃ | — | pyrazole (H, CH₃, H₅C₂, OH) | logP = 1.72ᵃ⁾ |
| 70 | 1 | (2) CH₂ | CH₃ | CH₃ | (4) CF₃ | — | 2-methyl-cyclohexane-1,3-dione | logP = 1.95ᵃ⁾ |
| 71 | 1 | (2) CH₂ | CH₃ | CH₃ | (4) CF₃ | — | pyrazole (H, CH₃, H₅C₂, OH) | logP = 1.77ᵃ⁾ |

The logP values given in Table 1 were determined in accordance with EEC directive 79/831 Annex V.A8 by HPLC (High Performance Liquid Chromatography) on a reversed-phase column (C 18). Temperature: 43° C.

(a) Mobile phases for the determination in the acidic range: 0.1% aqueous phosphoric acid, acetonitrile; linear gradient of 10% acetonitrile to 90% acetonitrile—the corresponding data in Table 1 are labelled a).

(b) Mobile phases for the determination in the neutral range: 0.01 molar aqueous phosphate buffer solution, acetonitrile, linear gradient from 10% acetonitrile to 90% acetonitrile—the corresponding data in Table 1 are labelled$^b$).

Calibration was carried out using unbranched alkan-2-ones (with 3 to 16 carbon atoms) whose logP values are known (determination of the logP values by the retention times using linear interpolation between two successive alkanones).

The lambda-max values were determined in the maxima of the chromatographic signals using the UV spectra from 200 nm to 400 nm.

The compound listed above in Table 1 as Example 3 can be prepared, for example, as follows:

(Process (c))

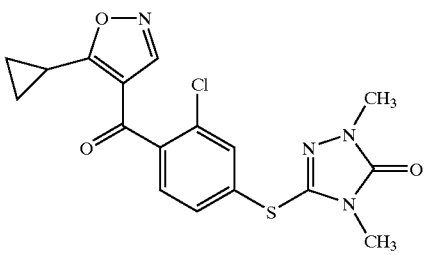

A mixture of 5.0 g (13.7 mmol) of 1-[2-chloro-4-[(4,5-dihydro-1,4-dimethyl-5-oxo-1H-1,2,4-triazol-3-yl)-sulphanyl]-phenyl]-3-cyclopropyl-1,3-propanedione (cf. Example 67), 1.5 g (17 mmol) of N,N-dimethyl-formamide dimethyl acetal and 50 ml of toluene is stirred at 90° C. for 18 hours and then concentrated under water pump vacuum. The residue is taken up in 50 ml of ethanol and admixed with 0.95 g (13.7 mmol) of hydroxylamine hydrochloride. The reaction mixture is then stirred at room temperature (approximately 20° C.) for 2 hours and subsequently concentrated under water pump vacuum. The residue is shaken with water/methylene chloride and the organic phase is washed with saturated aqueous sodium chloride solution, dried with sodium sulphate and filtered. The filtrate is concentrated under water pump vacuum and the residue is purified by column chromatography (silica gel, cyclohexane/ethyl acetate, vol.: 7:3):

This gives 0.13 g (2.5% of theory) of 5-[3-chloro-4-[(5-cyclopropyl-isoxazol-4-yl)-carbonyl]-phenylsulphanyl]-2, 4-dihydro-2,4-dimethyl-3H-1,2,4-triazol-3-one.

The compound listed above in Table 1 as Example 22 can be prepared, for example, as follows:

(Subsequent reaction)

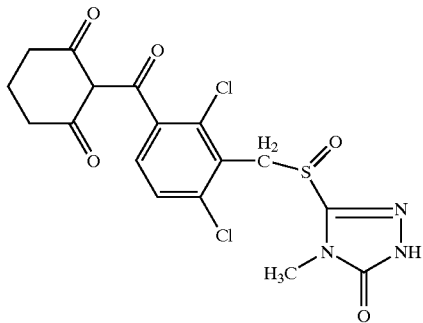

1.4 g (3 mmol) of 2-[2,4-dichloro-3-[(4-methyl-5-oxo-4, 5-dihydro-1H-1,2,4-triazol-3-yl)-sulphanylmethyl]-benzoyl]-1,3-cyclohexanedione (cf. Example 18) are initially charged in 100 ml of methylene chloride and admixed with 0.35 g (7.5 mmol) of formic acid, 1.1 g of aqueous hydrogen peroxide (30% strength, i.e. 9 mmol of $H_2O_2$) and a spatula tip of ammonium molybdate. The reaction mixture is stirred at room temperature (approximately 20° C.) for 24 hours, subsequently washed with water, then with 1 N aqueous sodium hydroxide solution and again with water and finally with saturated aqueous sodium chloride solution, dried with sodium sulphate and filtered. From the filtrate, the solvent is carefully distilled off under reduced pressure.

This gives 1.0 g (75% of theory) of 2-[2,4-dichloro-3-[(4-methyl-5-oxo-4,5-dihydro-1H-1,2,4-triazol-3-yl)-sulphinylmethyl]-benzoyl]-1,3-cyclohexanedione.

The compound listed above in Table 1 as Example 67 can be prepared, for example, as follows:

(Process (a))

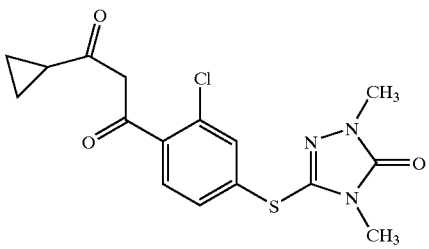

3.7 g (44 mmol) of cyclopropyl methyl ketone arc initially charged in 50 ml of acetone and admixed with 1.32 g of sodium hydride (75% pure, 44 mmol of NaH). The mixture is stirred at room temperature (approximately 20° C.) for 30 minutes and then admixed with a suspension of 8.0 g (22 mmol) of 2,2-dimethyl-propyl 2-chloro-4-[(4,5-dihydro-1, 4-dimethyl-5-oxo-1H-1,2,4-triazol-3-yl)-sulphanyl]-benzoate—cf. Example (II-4)—and 1 g of dibenzo-18-crown-6 in 40 ml of acetone. The reaction mixture is heated under reflux for 60 minutes and, after cooling to room temperature, admixed with approximately the same amount by volume of saturated aqueous ammonium chloride solution and then shaken with ethyl acetate. The organic phase is dried with sodium sulphate and filtered. From the filtrate, the solvent is carefully distilled off under reduced pressure.

This gives 6.0 g (75% of theory) of 1-[2-chloro-4-[(4,5-dihydro-1,4-dimethyl-5-oxo-1H-1,2,4-triazol-3-yl)-sulphanyl]-phenyl]-3-cyclopropyl-1,3-propanedione.

Starting Materials of the Formula (II)

EXAMPLE (II-1)

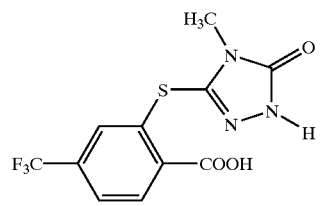

A mixture of 2.0 g (6.7 mmol) of 2-[(4-methyl-5-oxo-4, 5-dihydro-1H-1,2,4-triazol-3-yl)-sulphanyl]-4-trifluoromethyl-benzonitrile and 25 ml of 48% strength aqueous hydrobromic acid is heated at 40° C. for 5 hours. The yellow suspension is diluted with 10 ml of water and filtered. At 50° C., the residue is stirred with 40 ml of saturated aqueous sodium bicarbonate solution, and undissolved solid is filtered off. The filtrate is acidified with 2 N hydrochloric acid and the resulting precipitate is filtered off and dried under reduced pressure.

This gives 1.0 g (47% of theory) of 2-[(4-methyl-5-oxo-4,5-dihydro-1H-1,2,4-triazol-3-yl)-sulphanyl]-4-trifluoromethyl-benzoic acid of melting point 229° C.

EXAMPLE (II-2)

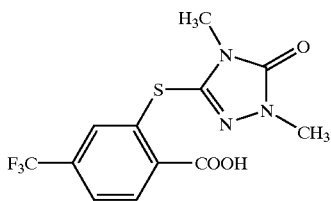

A mixture of 3.0 g (9.5 mmol) of 2-[(1,4-dimethyl-5-oxo-4,5-dihydro-1H-1,2,4-triazol-3-yl)-sulphanyl]-4-trifluoromethyl-benzonitrile and 30 ml of 48% strength aqueous hydrobromic acid is heated at 95° C. for 12 hours. The suspension is diluted with 20 ml of water and filtered. At 50° C., the residue is stirred with 40 ml of saturated aqueous sodium bicarbonate solution and undissolved solid is filtered off. The filtrate is acidified with 2N hydrochloric acid and the resulting precipitate is filtered off and dried under reduced pressure.

This gives 1.85 g (58% of theory) of 2-[(1,4-dimethyl-5-oxo-4,5-dihydro-1H-1,2,4-triazol-3-yl)-sulphanyl]-4-trifluoromethyl-benzoic acid of melting point 211° C.

EXAMPLE (II-3)

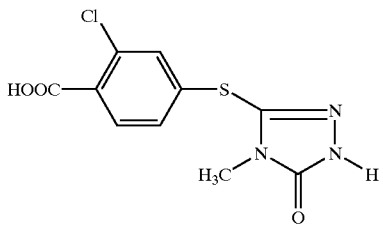

5.4 g (15 mmol) of 2,2-dimethyl-propyl 2-chloro-4-[(4,5-dihydro-4-methyl-5-oxo-1H-1,2,4-triazol-3-yl)-sulphanyl]-benzoate are, in a mixture of 50 ml of dioxane, 50 ml of water and 1.2 g (30 mmol) of sodium hydroxide, heated at 80° C. for 60 minutes. The mixture is then diluted with 100 ml of water, acidified to pH=2 using conlc. hydrochloric acid and then admixed with methylene chloride. The resulting crystalline product is isolated by filtration with suction.

This gives 2.9 g (67% of theory) of 2-chloro-4-[(4,5-dihydro-4-methyl-5-oxo-1H-1,2,4-triazol-3-yl)-sulphanyl]-benzoic acid of melting point 236° C.

EXAMPLE (II-4)

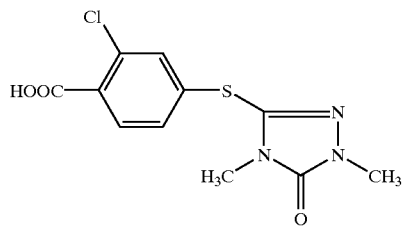

7.4 g (20 mmol) of 2,2-dimethyl-propyl 2-chloro-4-[(4,5-dihydro-1,4-dimethyl-5-oxo-1H-1,2,4-triazol-3-yl)-sulphanyl]-benzoic acid are, in a mixture of dioxane, 50 ml of water and 1 g (25 mmol) of sodium hydroxide, heated with stirring at 80° C. for 60 minutes. The mixture is then concentrated under water pump vacuum to about half its original volume, diluted with 100 ml of water and acidified with 10% strength hydrochloric acid. The resulting crystalline product is isolated by filtration This gives 4.9 g (81% of theory) of 2-chloro-4-[(4,5-dihydro-1,4-dimethyl-5-oxo-1H-1,2,4-triazol-3-yl)-sulphanyl]-benzoic acid of melting point 222° C.

Analogously to Examples (II-1) to (II-4), it is also possible to prepare, for example, the compounds of the general formula (II) listed in Table 2 below.

TABLE 2

(II)

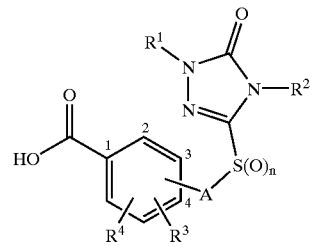

Examples of compounds of the formula (II)

| Ex. No. | n | (position) A | $R^1$ | $R^2$ | (position) $R^3$ | (position) $R^4$ | Physical data |
|---|---|---|---|---|---|---|---|
| II-5 | 2 | (4) — | H | $CH_3$ | (2) Cl | — | m.p.: 285° C. |
| II-6 | 2 | (4) — | $CH_3$ | $CH_3$ | (2) Cl | — | m.p.: 298° C. |
| II-7 | 0 | (3) $CH_2$ | H | $CH_3$ | (2) Cl | (4) Cl | m.p.: 227° C. |

TABLE 2-continued

Examples of compounds of the formula (II)

| Ex. No. | n | (position) A | R¹ | R² | (position) R³ | (position) R⁴ | Physical data |
|---|---|---|---|---|---|---|---|
| II-8 | 0 | (3) CH₂ | CH₃ | CH₃ | (2) Cl | (4) Cl | m.p.: 203° C. |
| II-9 | 0 | (2) CH₂ | CH₃ | CH₃ | (4) CF₃ | — | logP = 1.94[a)] |
| II-10 | 0 | (4) — | C₂H₅ | CH₃ | (2) Cl | — | m.p.: 168° C. |
| II-11 | 0 | (4) — | n-C₃H₇ | CH₃ | (2) Cl | — | m.p.: 172° C. |
| II-12 | 0 | (4) — | H₂C=CH-CH₂- | CH₃ | (2) Cl | — | m.p.: 160° C. |
| II-13 | 0 | (4) — | CH≡C-CH₂- | CH₃ | (2) Cl | — | m.p.: 153° C. |
| II-14 | 0 | (4) — | cyclopropyl-CH₂- | CH₃ | (2) Cl | — | m.p.: 172° C. |
| II-15 | 0 | (4) — | benzyl-CH₂- | CH₃ | (2) Cl | — | m.p.: 177° C. |

The compound listed above in Table 2 as Example (II-9) can, for example, be prepared as follows:

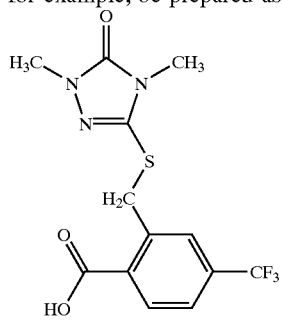

11.5 g (31.9 mmol) of methyl 2-[(4,5-dihydro-1,4-dimethyl-5-oxo-1H-1,2,4-triazol-3-yl)-sulphanylmethyl]-4-trifluoromethyl-benzoate are initially charged in 200 ml of cyclohexane and admixed with 50 ml of 2-methoxy-ethanol and then with 1.8 g of potassium hydroxide. The reaction mixture is stilled at room temperature (approximately 20° C.) for 2 hours and then poured into 200 ml of water. After shaking with 2N hydrochloric acid, the resulting crystalline product is isolated by filtration with suction.

This gives 7.5 g (68% of theory) of 2-[(4,5-dihydro-1,4-dimethyl-5-oxo-1H-1,2,4-triazol-3-yl)-sulphanylmethyl]-4-trifluoromethyl-benzoic acid.

Intermediates of the Formula (VI)

EXAMPLE (VI-1)

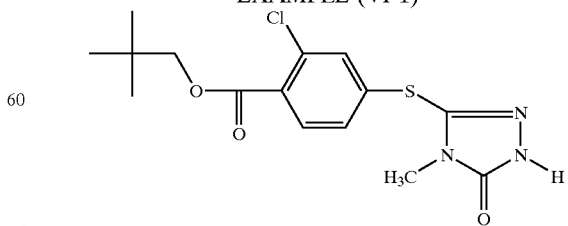

48.4 g (0.20 mol) of neopentyl 4-amino-2-chloro-benzoate (cf. DE-A-2 445 529) are taken up in 100 ml of water and, with stirring, admixed dropwise with 100 g of conc. hydrochloric acid. At −5° C., a solution of 14.1 g (0.20 mol) of sodium nitrite in 40 ml of water is added dropwise with stirring to the above mixture. The resulting solution is then quickly added dropwise with vigorous stirring to a mixture of 26.2 g (0.20 mol) of 5-mercapto-4-methyl-2,4-dihydro-1,2,4-triazol-3-one, 8.0 g (0.20 mol) of sodium hydroxide, 40.8 g (0.3 mol) of sodium acetate trihydrate, 2 g of copper(II) chloride dihydrate, 300 ml of water and 300 ml of methylene chloride, a temperature increase to about 30° C. and evolution of gas being observed. After 30 minutes of stirring, the organic phase is separated off, washed with water, dried with sodium sulphate and filtered. The filtrate is concentrated under water pump vacuum and the residue is recrystallized from diisopropyl ether.

This gives 26.7 g (37% of theory) of 2,2-dimethyl-propyl 2-chloro-4-[(4,5-dihydro-4-methyl-5-oxo-1H-1,2,4-triazol-3-yl)-sulphanyl]-benzoate of melting point 138° C.

EXAMPLE (VI-2)

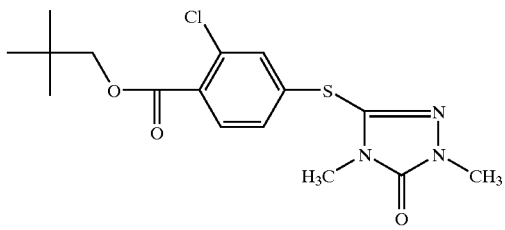

21.4 g (60 mmol) of 2,2-dimethyl-propyl 2-chloro-4-[(4,5-dihydro-4-methyl-5-oxo-1H-1,2,4-triazol-3-yl)-sulphanyl]-benzoate are taken up in 150 ml of acetone and, with 13.8 g (0.1 mol) of potassium carbonate and 14.2 g (0.1 mol) of iodomethane, heated under reflux for 16 hours. The mixture is then concentrated under water pump vacuum and the residue is taken up in methylene chloride and acidified slightly using 1N hydrochloric acid. The organic phase is once again washed with water and with saturated aqueous sodium chloride solution, dried with sodium sulphate and filtered. The filtrate is concentrated under water pump vacuum, the residue is digested with petroleum ether and the resulting crystalline product is isolated by filtration with suction.

This gives 20.5 g (92% of theory) of 2,2-dimethyl-propyl 2-chloro-4-[(4,5-dihydro-1,4-dimethyl-5-oxo-1H-1,2,4-triazol-3-yl)-sulphanyl]-benzoate of melting point 101° C.

EXAMPLE (VI-3)

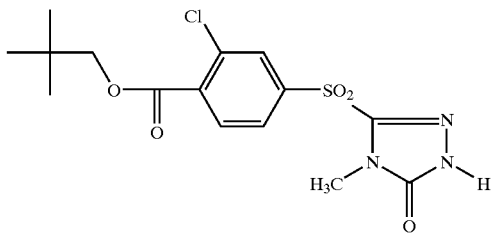

3.6 g (10 mmol) of 2,2-dimethyl-propyl 2-chloro-4-[(4,5-dihydro-4-methyl-5-oxo-1H-1,2,4-triazol-3-yl)-sulphanyl]-benzoate are taken up in 150 ml of methylene chloride and admixed with 10 g of 3-chloro-perbenzoic acid. After 16 hours of stirring at 20° C., the mixture is washed with aqueous sodium hydrogen sulphite solution, then with water and finally with saturated aqueous sodium chloride solution. The organic phase is concentrated under water pump vacuum, the residue is digested with diethyl ether and the resulting crystalline product is isolated by filtration with suction.

This gives 3.3 g (85% of theory) of 2,2-dimethyl-propyl 2-chloro-4-[(4,5-dihydro-4-methyl-5-oxo-1H-1,2,4-triazol-3-yl)-sulphonyl]-benzoate of melting point 177° C.

EXAMPLE (VI-4)

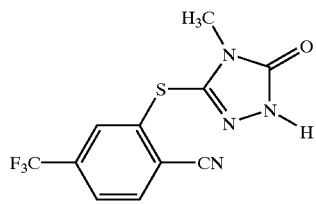

Over a period of 2 hours, 14 g (65 mmol) of 2-nitro-4-trifluoromethyl-benzonitrile are added to a mixture of 10 g (76 mmol) of 4-methyl-5-sulphinyl-2,4-dihydro-3H-1,2,4-triazol-3-one and 22.5 g (163 mmol) of potassium carbonate in 100 ml of dimethyl sulphoxide. After 4 hours of stirring at 50° C., most of the solvent is removed under reduced pressure and the residue is introduced into water. The precipitated solid is filtered off, dried and recrystallized from n-propanol.

This gives 6.5 g (33% of theory) of 2-[(4-methyl-5-oxo-4,5-dihydro-1H-1,2,4-triazol-3-yl)-sulphanyl]-4-trifluoromethyl-benzonitrile of melting point 182° C. (with decomp.).

EXAMPLE (VI-5)

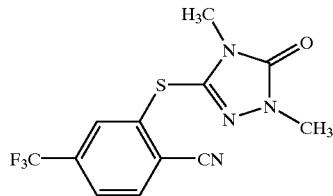

2.5 g (17.6 mmol) of iodomethane are added to a mixture of 5.0 g (16.7 mmol) of 2-[(4-methyl-5-oxo-4,5-dihydro-1H-1,2,4-triazol-3-yl)-sulphanyl]-4-trifluoromethyl-benzonitrile and 4.6 g (33.4 mmol) of potassium carbonate in 50 ml of acetonitrile, and the reaction mixture is heated at 50° C. for 6 hours. The solvent is then removed under reduced pressure and the oily residue is taken up in water and dichloro-methane. The organic phase is separated off and dried over magnesium sulphate, and the solvent is removed under reduced pressure.

This gives 5.1 g, (97% of theory) of 2-[(1,4-dimethyl-5-oxo-4,5-dihydro-1H-1,2,4-triazol-3-yl)-sulphanyl]-4-trifluoromethyl-benzonitrile of melting point 113° C.

Analogously to Examples (VI-1) to (VI-5), it is also possible to prepare, for example, the compounds of the general formula (VI) listed in Table 3 below.

TABLE 3

(VI)

Examples of compounds of the formula (VI)

| Ex. No. | n | (position) A | R¹ | R² | (position) R³ | (position) R⁴ | Y | Physical data |
|---|---|---|---|---|---|---|---|---|
| VI-6 | 2 | (4) — | CH₃ | CH₃ | (2) Cl | — | tert-butyl acetate group | m.p.: 114° C. |
| VI-7 | 0 | (3) CH₂ | H | CH₃ | (2) Cl | (4) Cl | methyl acetate group | m.p.: 111° C. |
| VI-8 | 0 | (3) CH₂ | CH₃ | CH₃ | (2) Cl | (4) Cl | methyl acetate group | logP = 2.12ᵃ⁾ |
| VI-9 | 0 | (4) — | C₂H₅ | CH₃ | (2) Cl | — | tert-butyl acetate group | logP = 3.80ᵃ⁾ |
| VI-10 | 0 | (4) — | n-C₃H₇ | CH₃ | (2) Cl | — | tert-butyl acetate group | logP = 4.19ᵃ⁾ |
| VI-11 | 0 | (4) — | H₂C=CH-CH₂- | CH₃ | (2) Cl | — | tert-butyl acetate group | logP = 3.92ᵃ⁾ |
| VI-12 | 0 | (4) — | HC≡C-CH₂- | CH₃ | (2) Cl | — | tert-butyl acetate group | logP = 3.70ᵃ⁾ |
| VI-13 | 0 | (4) — | cyclopropylmethyl | CH₃ | (2) Cl | — | tert-butyl acetate group | logP = 4.27ᵃ⁾ |
| VI-14 | 0 | (4) — | benzyl | CH₃ | (2) Cl | — | tert-butyl acetate group | logP = 4.51ᵃ⁾ |
| VI-15 | 0 | (2) — | CH₃ | CH₃ | (4) CF₃ | — | CN | m.p.: 113° C. |

TABLE 3-continued

Examples of compounds of the formula (VI)

| Ex. No. | n | (position) A | R¹ | R² | (position) R³ | (position) R⁴ | Y | Physical data |
|---|---|---|---|---|---|---|---|---|
| VI-16 | (2) | CH₂ | CH₃ | CH₃ | (4) CF₃ | — | 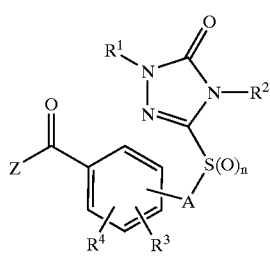 | logP = 2.48[a)] |

Use Examples

Example A
Pre-emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is sprayed with the preparation of active compound such that the particular amount of active compound desired is applied per unit area. The concentration of active compound in the spray liquor is chosen so that the particular amount of active compound desired is applied in 1000 litres of water per hectare.

After three weeks, the degree of damage to the plants is rated in % damage in comparison to the development of the untreated control. The figures denote:
0%=no effect (like untreated control)
100%=total destruction In this test, for example, the compounds of Preparation Examples 1 and 15 exhibit strong activity against weeds, and they are tolerated well by some crop plants, such as, for example, cotton, maize, soya and wheat.

Example B
Post-emergence Test
Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants of a height of 5 to 15 cm are sprayed with the preparation of active compound such that the particular amounts of active compound desired are applied per unit area. The concentration of the spray liquor is chosen so that the particular amounts of active compound desired are applied in 1000 l of water/ha.

After three weeks, the degree of damage to the plants is rated in % damage in comparison to the development of the untreated control. The figures denote:
0%=no effect (like untreated control)
100%=total destruction In this test, for example, the compounds of Preparation Examples 1 and 15 exhibit strong activity against weeds, and they are tolerated well by crop plants, such as, for example, maize.

What is claimed is:

1. A substituted aryl ketone of the formula (I)

wherein
n represents the numbers 0, 1 or 2,
A represents a single bond or represents alkanediyl,
R¹ represents hydrogen or represents optionally substituted alkyl, alkenyl, alkynyl, cycloalkyl, cycloalkylalkyl, aryl or arylalkyl,
R² represents hydrogen, amino, or represents optionally substituted alkyl, alkoxy, alkylamino, dialkylamino, alkenyl, alkenyloxy, alkynyl, alkynyloxy, cycloalkyl, cycloalkylalkyl, aryl, arylamino or arylalkyl,
R³ represents hydrogen, nitro, cyano, carboxyl, carbamoyl, thiocarbamoyl, halogen, or represents optionally substituted alkyl, alkylcarbonyl, alkoxy, alkoxycarbonyl, alkylthio, alkylsulphinyl, alkylsulphonyl, alkylamino, dialkylamino or dialkylaminosulphonyl,
R⁴ represents hydrogen, nitro, cyano, carboxyl, carbamoyl, thiocarbamoyl, halogen, or represents optionally substituted alkyl, alkylcarbonyl, alkoxy, alkoxycarbonyl, alkylthio, alkylsulphinyl, alkylsulphonyl, alkylamino, dialkylamino or dialkylaminosulphonyl, and Z represents

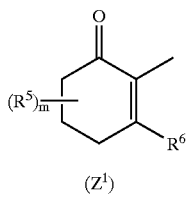

(Z¹)

wherein
  m represents the numbers 0 to 6,
  $R^5$ represents halogen or represents optionally substituted alkyl or alkylthio, or—if m represents 2—together with a second radical $R^5$ represents alkyanediyl (alkylene), and
  $R^6$ represents hydroxyl, formyloxy, or represents optionally substituted alkoxy, alkylthio, alkylcarbonyloxy, alkoxycarbonyloxy, alkylaminocarbonyloxy, alkylsulphonyloxy, alkenyloxy, alkynyloxy, arylalkyl, aryloxy, arylthio, arylcarbonyloxy, arylcarbonylalkoxy, arylsulphonyloxy, arylalkoxy, or arylalkylthio,
including all possible tautomeric forms of the compounds of the formula (I) and the possible salts of the compounds of the formula (I).

2. The compound of claim 1, wherein
  A represents a single bond or represents alkanediyl having 1 to 6 carbon atoms,
  $R^1$ represents hydrogen, represents optionally cyano-, halogen- or $C_1$–$C_4$-alkoxy-substituted alkyl having 1 to 6 carbon atoms, represents optionally cyano- or halogen-substituted alkenyl or alkynyl having 2 to 6 carbon atoms, represents optionally cyano-, halogen- or $C_1$–$C_4$-alkyl-substituted cycloalkyl or cycloalkylalkyl having 3 to 6 carbon atoms in the cycloalkyl group and optionally 1 to 4 carbon atoms in the alkyl moiety, or represents optionally nitro-, cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted aryl or arylalkyl having 6 or 10 carbon atoms in the aryl group and optionally 1 to 4 carbon atoms in the alkyl moiety,
  $R^2$ represents hydrogen, amino, represents optionally cyano-, halogen- or $C_1$–$C_4$-alkoxy-substituted alkyl, alkoxy, alkylamino or di-alkylamino having 1 to 6 carbon atoms in the alkyl groups, represents optionally cyano- or halogen-substituted alkenyl, alkenyloxy, alkynyl or alkynyloxy having 2 to 6 carbon atoms, represents optionally cyano-, halogen- or $C_1$–$C_4$-alkyl-substituted cycloalkyl or cycloalkylalkyl having 3 to 6 carbon atoms in the cycloalkyl group and optionally 1 to 4 carbon atoms in the alkyl moiety, or represents optionally nitro-, cyano-, halogen-, $C_1$–$C_4$-alkyl-, $C_1$–$C_4$-halogenoalkyl-, $C_1$–$C_4$-alkoxy- or $C_1$–$C_4$-halogenoalkoxy-substituted aryl, arylamino or arylalkyl having 6 or 10 carbon atoms in the aryl group and optionally 1 to 4 carbon atoms in the alkyl moiety,
  $R^3$ represents hydrogen, nitro, cyano, carboxyl, carbamoyl, thiocarbamoyl, halogen, or represents optionally cyano-, halogen- or $C_1$–$C_4$-alkoxy-substituted alkyl, alkylcarbonyl, alkoxy, alkoxycarbonyl, alkylthio, alkylsulphinyl, alkylsulphonyl, alkylamino, dialkylamino or dialkylamino-sulphonyl having 1 to 6 carbon atoms in the alkyl groups, and
  $R^4$ represents hydrogen, nitro, cyano, carboxyl, carbamoyl, thiocarbamoyl, halogen, or represents optionally cyano-, halogen- or $C_1$–$C_4$-alkoxy-substituted alkyl, alkylcarbonyl, alkoxy, alkoxycarbonyl, alkylthio, alkylsulphinyl, alkylsulphonyl, alkylamino, dialkylamino or dialkylamino-sulphonyl having 1 to 6 carbon atoms in the alkyl groups.

3. The compound of claim 1, wherein
  m represents the numbers 0, 1, 2, 3 or 4,
  $R^5$ represents halogen or represents optionally cyano-, halogen- or $C_1$–$C_4$-alkoxy-substituted alkyl or alkylthio having 1 to 6 carbon atoms, or optionally also—if m represents 2—together with a second radical $R^5$ represents alkanediyl (alkylene) having 2 to 6 carbon atoms, and
  $R^6$ represents hydroxyl, formyloxy, or represents optionally cyano-, halogen- or $C_1$–$C_4$-alkoxy-substituted alkoxy, alkylthio, alkylcarbonyloxy, alkoxycarbonyloxy, alkylaminocarbonyloxy, or alkylsulphonyloxy having 1 to 6 carbon atoms in the alkyl groups, represents optionally cyano- or halogen-substituted alkenyloxy or alkynyloxy having 2 to 6 carbon atoms, or represents optionally nitro-, cyano-, halogen-, $C_1$–$C_4$-alkyl-, $C_1$–$C_4$-halogenoaklyl-, $C_1$–$C_4$alkoxy- or $C_1$–$C_4$-halogenoalkoxy-substituted arlyalkyl, aryloxy, arylthio, arylcarbonyloxy, arylcarbonylalkoxy, arylsulphonyloxy, arylalkoxy or arlyalkylthio having 6 or 10 carbon atoms in the aryl group and optionally 1 to 4 carbon atoms in the alkyl moiety.

4. The compound of claim 1, wherein
  A represents a single bond or represents alkanediyl having 1 to 4 carbon atoms,
  $R^1$ represents hydrogen, represents optionally cyano-, fluorine-, chlorine-, methoxy- or ethoxy-substituted methyl, ethyl, n- or i-propyl, n-, i-, s- or t-butyl, represents optionally cyano-, fluorine-, chlorine- or bromine-substituted propenyl, butenyl, propynyl or butynyl, represents optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, benzyl or phenylethyl,
  $R^2$ represents hydrogen, amino, represents optionally cyano-, fluorine-, chlorine-, methoxy- or ethoxy-substituted methyl, ethyl, n- or i-propyl, n-, i-, s- or t-butyl, methoxy, ethoxy, n- or i-propoxy, n-, i-, s- or t-butoxy, methylamino, ethylamino, n- or i-propylamino, n-, i- or s-butylamino, dimethylamino or diethylamino, represents optionally cyano-, fluorine-, chlorine- or bromine-substituted propenyl, butenyl, propenyloxy, butenyloxy, propynyl, butynyl, propynyloxy or butynyloxy, represents optionally cyano-, fluorine-, chlorine-, methyl- or ethyl-substituted cyclopropyl, cyclobutyl, cyclopentyl, cyclohexyl, cyclopropylmethyl, cyclobutylmethyl, cyclopentylmethyl or cyclohexylmethyl, or represents optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenyl, phenylamino, benzyl or phenylethyl, $R^3$ represents hydrogen, nitro, cyano, carboxyl, carbamoyl, thiocarbamoyl, fluorine, chlorine, bromine, or represents optionally cyano-, fluorine-, chlorine-, methoxy- or ethoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl or diethylaminosulphonyl, and $R^4$ represents hydrogen, nitro, cyano, carboxyl, carbamoyl, thiocarbamoyl, fluorine, chlorine, bromine, or represents optionally cyano-, fluorine-, chlorine-, methoxy- or ethoxy-substituted methyl, ethyl, n- or i-propyl, n-, i-, s- or t-butyl, acetyl, propionyl, n- or i-butyroyl, methoxy, ethoxy, n- or i-propoxy, n-, i-, s- or t-butoxy, methoxycarbonyl, ethoxycarbonyl, n- or i-propoxycarbonyl, methylthio, ethylthio, n- or i-propylthio, n-, i-, s- or t-butylthio, methylsulphinyl, ethylsulphinyl, n- or i-propylsulphinyl, methylsulphonyl, ethylsulphonyl, n- or i-propylsulphonyl, methylamino, ethylamino, n- or i-propylamino, n-, i-, s- or t-butylamino, dimethylamino, diethylamino, dimethylaminosulphonyl or diethylaminosulphonyl.

5. The compound of claim 1, wherein m represents the numbers 0, 1, 2 or 3, $R^5$ represents fluorine, chlorine, bromine, or represents optionally cyano-, fluorine-, chlorine-, methoxy- or ethoxy-substituted methyl, ethyl, n- or i-propyl, n-, i-, s- or t-butyl, methylthio, ethylthio, n- or i-propylthio, n-, i-, s- or t-butylthio, or optionally also—if m represents 2—together with a second radical $R^5$ represents ethane-1,2-diyl (dimethylene), propane-1,3-diyl (trimethylene) or butane-1,4-diyl (tetramethylene), and $R^6$ represents hydroxyl, formyloxy, represents optionally cyano-, fluorine-, chlorine-, methoxy- or ethoxy-substituted methoxy, ethoxy, n- or i-propoxy, n-, i-, s- or t-butoxy, methylthio, ethylthio, n- or i-propylthio, n-, i-, s- or t-butylthio, acetyloxy, propionyloxy, n- or i-butyroyloxy, methoxycarbonyloxy, ethoxycarbonyloxy, n- or i-propoxycarbonyloxy, methylaminocarbonyloxy, ethylaminocarbonyloxy, n- or i-propylaminocarbonyloxy, methylsulphonyloxy, ethylsulphonyloxy, n- or i-propylsulphonyloxy, represents optionally cyano-, fluorine-, chlorine- or bromine-substituted propenyloxy, butenyloxy, propynyloxy or butynyloxy, or represents optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy- or trifluoromethoxy-substituted phenoxy, phenylthio, benzoyloxy, benzoylmethoxy, phenylsulphonyloxy, phenylmethoxy, phenylmethylthio or benzyl.

6. A process for preparing the compound of claim 1 comprising reacting a substituted benzoic acid of the formula (II)

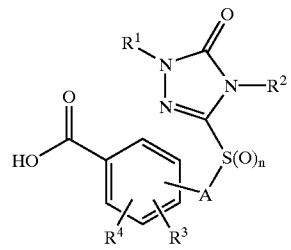

(II)

wherein n, A, $R^1$, $R^2$, $R^3$ and $R^4$ are as defined in claim 1 with a compound of the formula (III)

Z—H (III)

wherein Z is as defined in claim 1, and collecting the reaction product.

7. A composition comprising at least one compound of claim 1 and extenders.

8. A method of controlling the growth of at least one plant comprising applying a composition comprising at least one substituted aryl ketone of claim 1 to said plant.

* * * * *